United States Patent [19]

Ishii et al.

[11] Patent Number: 4,767,752

[45] Date of Patent: Aug. 30, 1988

[54] IMIDAZOLYL OR TRIAZOLYL SUBSTITUTED PROPIONATE DERIVATIVE AND NONMEDICAL FUNGICIDE CONTAINING THE SAME

[75] Inventors: Teruhiko Ishii; Haruaki Ito; Takashi Bando; Toshiro Yasue; Masatoshi Motoyoshi; Matsutaro Yamaguchi; Yutaka Wakatsuki; Nobuko Saito, all of Tokyo, Japan

[73] Assignee: S.D.S. Biotech K.K., Tokyo, Japan

[21] Appl. No.: 840,183

[22] Filed: Mar. 17, 1986

[30] Foreign Application Priority Data

Mar. 18, 1985 [JP] Japan .................................. 60-52533
Feb. 10, 1986 [JP] Japan .................................. 61-25694

[51] Int. Cl.$^4$ .................... A01N 43/50; A01N 43/653; C07D 233/60; C07D 249/08
[52] U.S. Cl. .................................... 514/184; 514/383; 514/399; 548/101; 548/262; 548/341
[58] Field of Search .................... 548/101, 262, 361; 514/184, 383, 399

[56] References Cited

U.S. PATENT DOCUMENTS 3,826,836  7/1974  Buchel et al. .................... 548/341 X
4,507,141  3/1985  Regel et al. .................... 514/383 X
4,584,008  4/1986  Cherpeck .................... 548/262 X

FOREIGN PATENT DOCUMENTS 0000752  2/1979  European Pat. Off. ............ 514/383

OTHER PUBLICATIONS

JP-A-55-118466, published Sep. 11, 1980, Abstract only.
JP-A-60-202868, published Oct. 14, 1985, Abstract only.
JP-A-5978163, published May 4, 1984, Abstract only.

Primary Examiner—Donald G. Daus
Assistant Examiner—Diana G. Rivers
Attorney, Agent, or Firm—Sughrue, Mion, Zinn, Macpeak & Seas

[57] ABSTRACT

A propionate derivative having the general formula (I):

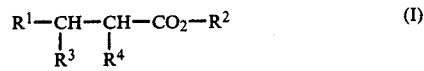

wherein $R^1$ is phenyl which may be substituted with one or more of the same as different substituents selected from the group consisting of halogen, methyl, methoxy, and nitro, $R^2$ is alkyl, cycloalkyl, or alkenyl, $R^3$ is alkylthio, cycloalkylthio, alkenylthio, phenylthio, or benzylthio which may be substituted with halogen or methyl and $R^4$ is imidazol-1-yl or 1,2,4-triazol-1-yl, or the acid addition salt thereof or the metal complex thereof.

This novel propionate derivative is suitable for use as an agricultural fungicide.

10 Claims, No Drawings

IMIDAZOLYL OR TRIAZOLYL SUBSTITUTED PROPIONATE DERIVATIVE AND NONMEDICAL FUNGICIDE CONTAINING THE SAME

BACKGROUND OF THE INVENTION

1. Field of the Invention

The present invention relates to a novel propionate derivative suitable for use as a nonmedical fungicide or germicide, especially for use as an agricultural fungicide. The present invention also relates to a nonmedical fungicide.

2. Description of the Related Art

It is disclosed, for example, in German Unexamined Patent Publication (i.e., DOS) Nos. 2908323.6 and 2908324.7 that triazole derivatives such as 2-phenyl-3,3-bis-triazolyl-propionic acid esters and 2-phenyl-3-triazolylpropenoic acid derivatives are fungicides with a curative effect against true mildews on fruit, vegetables and cereals and also in European Unexamined Patent Publication No. EP 104691A that pyridine derivatives such as 3-alkylthio-3-(2,4-dichlorophenyl)-2-(3-pyridyl)propionic acid esters are useful as fungicides against powdery mildews, blights and leaf-spot. However, these triazole and pyridine derivatives are not sufficient to fulfill the desired effects, especially referring to the fungicidal spectra.

SUMMARY OF THE INVENTION

Accordingly, the objects of the present invention are to provide novel compounds having the desired fungicidal or antibacterial activities.

Another object of the present invention is to provide effective nonmedical, especially agricultural fungicides.

Other objects and advantages of the present invention will be apparent from the following description.

In accordance with the present invention, there is provided a propionate derivative having the general formula (I):

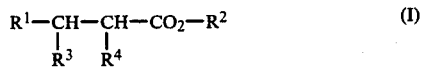

wherein $R^1$ is phenyl which may be substituted with one or more of the same or different substituents selected from the group consisting of halogen, methyl, methoxy, and nitro, $R^2$ is alkyl, cycloalkyl, or alkenyl, $R^3$ is alkylthio, cycloalkylthio alkenylthio, phenylthio, or benzylthio which may be substituted with halogen or methyl, and $R^4$ is imidazol-1-yl or 1,2,4-triazol-1-yl,
or the acid addition salt thereof or the metal complex thereof.

In accordance with the present invention, there is also provided a nonmedical fungicide comprising, as an effective ingredient, the propionate derivative having the above-mentioned general formula (I) or the agriculturally acceptable salt thereof, or the metal complex thereof having the above-mentioned general formula (II).

DESCRIPTION OF THE PREFERRED EMBODIMENTS

According to the present invention, these are provided novel propionate derivatives having the above-mentioned general formula (I). In the general formula (I), when $R^1$ represents substituted phenyl, the preferable $R^1$ groups are those substituted with 1 to 3 substituents, more preferably 1 or 2 substituents, which may be the same or different and which are selected from Cl, F, $OCH_3$, and $CH_3$. Typical examples of such substituents are 4-fluorophenyl, 4-chlorophenyl, 3,4-dichlorophenyl, 2,4-dichlorophenyl, and 2-chloro-6-fluorophenyl. The most preferable substituent $R^1$ is 2,4-dichlorophenyl.

The substituents $R^2$ in the general formula (I) are linear or branched alkyl groups preferably having 1 to 6 carbon atoms, more preferably 1 to 3 carbon atoms; cycloalkyl groups preferably having 3 to 7 carbon atoms, and alkenyl groups preferably having 3 to 6 carbon atoms.

The substituents $R^3$ in the general formula (I) are alkylthio groups preferably having 1 to 6 carbon atoms, cycloalkylthio groups preferably having 3 to 7 carbon atoms, alkenylthio groups preferably having 3 to 6 carbon atoms, or a phenylthio group or a benzylthio group which may be substituted with halogen or methyl. The preferable substituents $R^3$ are alkylthio groups having a linear or branched alkyl group with 1 to 4 carbon atoms.

The acid additive salts of the propionate derivatives (I) are those which are formed from the propionate derivatives (I) and strong acids. Examples of such strong acids are hydrochloric acid, hydrobromic acid, sulfuric acid, oxalic acid, and sulfonic acid.

The metal complexes of the propionate derivatives (I) are those which are composed of the propionate derivaties (I) and the inorganic acid salts of metals such as copper, cobalt, zinc, nickel, iron, and silver. The metal complexes can be represented by, for example, the following general formula (I'):

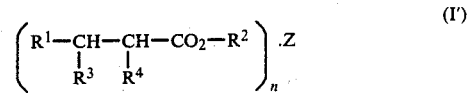

wherein $R^1$, $R^2$, $R^3$, and $R^4$ are as defined above and Z is a metal salt, and n is an integer of 1 to 4. The typical examples of the metal salts Z are copper (II) chloride, copper (II) bromide, copper (II) sulfate, cobalt (II) bromide, zinc chloride, nickel (II) chloride, iron (II) chloride, cobalt (II) chloride, and silver nitrate.

The novel propionate derivatives having the general formula (I) according to the present invention can be prepared as follows:

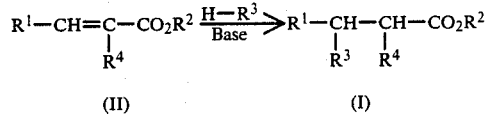

Thus, typically, olefins having the general formula (II) are allowed to react with a thiol $R^3$—H in the presence of a catalytic amount of a base such as piperidine. The reaction is generally carried out in an alcohol upon heating at an approximate boiling point of the solvent for, for example, 24 hours. Alternatively, an alcolate $R^2$—ONa is suspended in diethyl ether and thiol $R^3$—H is then added thereto, followed by gradually adding the olefin (II). The mixture is stirred at room temperature for 24 hours. The reactions are preferably carried out under a nitrogen atmosphere. The desired product (I) can be isolated and purified in any conventional manner.

The olefin (II) can be conventionally prepared in accordance with the following reaction scheme:

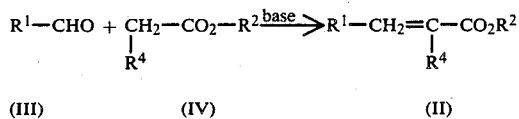

(III)    (IV)    (II)

In the typical reaction, the aldehyde (III) and the compound (IV) are heated in the presence of anhydrous potassium carbonate at a temperature of 50° C. to 90° C. in acetic anhydride. Alternatively, the olefin (II) can be prepared as follows:

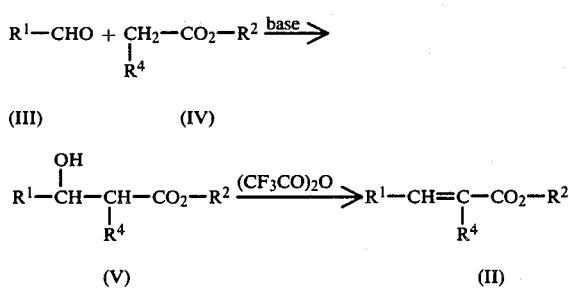

Thus, the compound (V) can be prepared from the aldehyde (III) and the compound (IV) by using a suitable base (e.g., a catalytic amount of sodium methoxide, sodium ethoxide, or potassium t-butoxide). The resultant compound (V) is reacted with trifluoroacetic anhydride in anhydrous tetrahydrofuran at room temperature to the boiling point of the solvent. The resultant compound (II) can be isolated and purified in any conventional manner.

The compounds represented by the general formula (I) have two asymmetric centers and are present as two pairs of diastereomers.

The acids capable of forming the agriculturally acceptable nontoxic salts (i.e., acid addition salts) of the compounds according to the present invention are strong acids such as hydrochloric acid, hydrobromic acid, sulfuric acid, oxalic acid, and sulfonic acid. The desired salts can be formed in any conventional manner. For example, an equimolar amounts of the free base and the desired acid in the solution thereof can be mixed. When the resultant salt is insoluble, it can be separated by filtration or evaporation of the solvent.

The metal complexes of the propionate derivative having the above-mentioned general formula (I') can be prepared by reacting the compound (I) with a metal salt in an inert solvent such as ethanol, methanol, propanol, chloroform, acetone, acetonitrile, and diethyl ether. Thus, the compound (I) is dissolved in the inert organic solvent and the desired metal salt is then added, followed by stirring at room temperature. As a result, the desired metal complex can be obtained. Examples of the cationic ions are aluminum, manganese, cobalt, iron, nickel, copper, zinc, silver, and cadmium ions. Examples of the counter anions are chlorine, bromine, iodine, sulfate, phosphate, nitrate, and carbonate, acetate ions. The formation of the complex salt is determined by an elemental analysis and atomic absorption method.

The compounds (I) have two asymmetric carbon atoms and, therefore, four stereo isomers are present. These isomers and the complex salts thereof are within the scope of the present invention. The preferred metal complexes of the propionate derivatives are those having the above-mentioned formula (I') wherein $R^1$ is phenyl substituted with one or two chlorine atoms, $R^2$ is alkyl having 1 to 6 carbon atoms, cycloalkyl having 3 to 7 carbon atoms, or alkenyl having 3 to 6 carbon atoms, $R^3$ is alkylthio having 1 to 6 carbon atoms, cycloalkylthio having 3 to 7 carbon atoms, or alkenylthio having 3 to 6 carbon atoms, Z is copper (II) chloride, copper (II) bromide, copper (II) sulfate, cobalt (II) bromide, zinc chloride, nickel (II) chloride, iron (II) chloride, cobalt (II) chloride, and silver nitrate.

According to the present invention, the propionate derivatives having the general formula (I) and the agriculturally acceptable salts thereof as well as the metal complexes of the propionate derivatives having the general formula (II) can be formulated, together with any additives including agriculturally acceptable diluents and carriers conventionally used in agricultural fungicide, to give agricultural fungicides. These fungicides can be advantageously used for treating plants or seeds, which have been infected by fungi.

The propionate derivatives having the general formula (I) exhibit preventive, therepeutic, or systemic fungicidal activities against various phytopathogens. Examples of such phytopathogenes are powdery mildew of wheats (*Erysiphe graminis* f. sp. *tritici*), rust of wheats (*Puccinia gramimis Puccinia recondita*), loose smut of wheat (*Usfilago tritici*), ice spot of wheat (*Pseudocercosporella herpotrichoides*), brown rot of apple (*Sclerotinia mali*), scab of pear (*Venturia nashicola*), black spot of pear (*Alternaria kikuchiana*), powdery mildew of cucurbit (*Sphaerotheca fuliginea*), rust of stone-leek (*Puccinia allii*), powdery mildew of pea (*Erysiphe pisi*), powdery mildew of rose (*Sphaerotheca pannosa*), gray mold of various crops (*Botrytis cinerea*), stem rot of various crops (*Solerotinia sclerotiorum*).

When the propionate derivatives having the general formula (I) are used as agricultural or horticultural fungicides, the compounds may be directly used. However, the present compounds can be formulated with solid carriers, liquid carriers, surfactants, and other conventional additives to form various forms of preparations such as emulsions, wettable powder, suspensions, and tablets. The present propionate derivatives can be formulated as an effective ingredient into the preparations in an amount of 0.1% to 99.9% by weight, preferably 0.2% to 80% by weight.

Examples of solid carriers usable in the formulation are finely divided powder or particles of kaolin clay, attapulgite clay, bentonite, acid clay, pyrophyllite, talc, diatomaceous earth, calcite, and white carbon. Examples of liquid carriers are aromatic hydrocarbons such as xylene and naphthalene; alcohols such as isopropanol, ethylene glycol, and cellosolve; ketones such as acetone, cyclohexanone, and isophorone; vegetable oil such as bean oil and cotton seed oil; dimethyl sulfoxide; and acetonitrile.

Examples of the surfactants usable as an emulsifier, dispersing agent and/or wetting and spreading agent are anionic surfactants such as alkyl sulfate salts, alkyl(aryl)sulfonate salts, dialkylsulfo succinate salts, polyoxyethylene alkyl aryl ether phosphate salts, and napthalene sulfonic acid folmaldehyde condensates; and nonionic surfactants such as polyoxyethylene polyoxypropylene block copolymers, and sorbitan fatty acid esters.

Examples of the formulation acids are lignin sulfonate, alginates, polyvinyl alcohol, gum arabic, carboxymethyl cellulose, and acidic isopropyl phosphate. It should be also noted that the active component of the present fungicide can be also formulated into the preparations together with one or more agents such as various conventional insecticides, bactericides, fungicides, herbicides, plant growth regulaters, miticides, nematocides, attractants, repellents, nutrients, fertilizers, and soil structure conditioning agents. Thus, these preparations are expected to exhibit various wide effects.

EXAMPLE

The present invention will be further explained by, but is by no means limited to, the following Synthetic Examples, Formulation Examples, and Test Examples. In Synthetic Examples, m, q, t, d, and s, in the NMR data represent multiplet, quartet, triplet, doublet, and singlet, respectively and the IR represents the specific absorption bands (cm$^{-1}$) of the infrared absorption spectra.

SYNTHETIC EXAMPLE 1

Synthesis of ethyl 3-(2,4-dichlorophenyl)-2-(1-imidazolyl)cinnamate (i.e., Starting Compound of Synthetic Example 2)

A 45 g amount of 2,4-dichlorobenzaldehyde and 39.8 g of ethyl 2-imidazolyl acetate were added to 300 ml of toluene, followed by the addition of 2 g of potassium tert-butoxide. The mixture was stirred under reflux for 18 hours. Thereafter, the solvent was distilled off in vacuo and n-hexane was added to the residue. The oily residue was gradually solidified and the n-hexane was removed by decantation. Acetone was added to the residue to obtain a white crystal. The resultant crystal was separated by suction filtration. The yield of white crystal was 44.7 g. The product obtained above was suspended in anhydrous tetrahydrofuran and 35 g of trifluoroacetic anhydride was dropwise added thereto. The mixture was heated under reflux for 5 hours.

The mixture was cooled to room temperature and the insoluble matter was separated by filtration. The resultant filtrate was poured into a large amount of water and was neutralized with a saturated aqueous sodium carbonate solution. The solution was extracted with dichloromethane and was dried over anhydrous sodium sulfate, followed by distilling off the solvent. The residue was then subjected to silica gel chromatography and was eluted with a 9:1 mixture of chloromethane and acetone. The desired product was obtained in the form of a pale yellow oil, which was gradually solidified (Yield=34.2 g).

The analytical results are as follows:
NMR: 7.95 ppm (s, imidazole 1H), 7.35—6.80 ppm (m, aromatic proton 3H and imidazol 2H), 6.40 ppm (d, J=10 Hz, methin proton 1H), 4.50—4.05 ppm (m, methylene proton 2H), 1.35 ppm (t, J=7 Hz, methyl proton 3H).

SYNTHETIC EXAMPLE 2

Synthesis of ethyl 3-(2,4-dichlorophenyl)-3-ethylthio-2-(1-imidazolyl)propionate (i.e., Compound No. 8)

A 6.8 g amount of sodium ethylate was dissolved in 100 ml of anhydrous diethyl ether and 6.2 g of ethanethiol was dropwise added thereto at room temperature. After the dropwise addition, the mixture was stirred at room temperature for 2 hours and, thereafter, 2.96 g of ethyl 3-(2,4-dichlorophenyl)-2-(1-imidazolyl)cinnamate was gradually added. After stirring the mixture at room temperature for 24 hours, 50 ml of water was added thereto and the mixture was stirred for 10 minutes, followed by extracting with ether. After washing the extract with water, the extract was dried over anhydrous sodium sulfate and the ether was distilled off. The resultant residue was subjected to silica-gel chromatography and was then eluted with a 95:5 mixture of chloroform and methanol.

The desired product was obtained in the form of a pale oil at a yield of 2.0 g (54%). The analytical results are as follows.
NMR: 7.45—6.80 ppm (m, imidazole proton 3H and aromatic proton 3H), 5.05—4.95 ppm (m, methine proton 2H), 4.40—3.95 ppm [q, methylene proton 2H (ester)], 2.70—2.05 ppm (m, methylene proton 2H), 1.45—1.00—ppm (m, terminal methyl proton 3H and 3H).

SYNTHESIS EXAMPLE 3

Synthesis of tert-butyl 3-(2,4-dichlorophenyl)-2-(1-imidazolyl)cinnamate (i.e., Starting Compound of Synthetic Example 4)

A 17.6 g amount of 2,4-dichlorobenzaldehye and 14 g of anhydrous potassium carbonate were added to 250 ml of acetic anhydride. Then, 18.2 g of tert-butyl 2-imidazolyl acetate was added, in a limited amount, to the mixture, while stirring at room temperature. The resultant mixture was stirred at a temperature of 60° C. for 3 hours. After the reaction, the reaction mixture was gradually added to warm water having a temperature of 50° C. and the mixture was stirred at the same temperature for a further 30 minutes. The reaction mixture was cooled to room temperature and the resultant mixture was neutralized with anhydrous potassium carbonate. Thereafter, the mixture was extracted with dichloromethane and, after washing with water, the mixture was dried over anhydrous sodium sulfate. The solvent was distilled off in vacuo and the residue was purified by silica-gel column chromatography. The desired product was eluted with a 9:1 mixture of dichloromethane and acetone. Thus, the desired product was obtained in the form of a yellow oil, which was gradually solidified. The yield was 18.6 g and the analytical results are as follows:
NMR: 7.85 ppm (s, imidazole proton 1H), 7.45—6.80 ppm (m, aromatic proton 3H and imidazole proton 2H), 6.30 ppm (d, J=9 Hz, methin proton 1H), 1.55 ppm (s, tert-butyl proton 9H).

SYNTHETIC EXAMPLE 4

Synthesis of tert-butyl 3-(2,4-dichlorophenyl)-3-isopropylthio-2-(1-imidazolyl)propionate (i.e., Compound No. 25)

A 3.39 g amount of tert-butyl 3-(2,4-dichlorophenyl)-2-(1-imidazolyl)cinnamate was dissolved in 50 ml of ethanol and, after 1 g of piperidine was dropwise added, 0.76 g of isopropyl mercaptan was added thereto. The mixture was stirred at a temperature of 60° C. to 70° C. for 24 hours. After the reaction, the reaction mixture was poured into a large amount of water and was extracted with methylene chloride. After washing with water, the extract was dried over anhydrous sodium sulfate. The solvent was distilled off in vacuo. The residue was purified by silica-gel column chromatography. The desired product in the form of a yellow oil was obtained by eluting with a 3:2 mixture of n-hexane and ethyl acetate.

The yield was 2.85 g (69%). The analytical results are as follows:

NMR: 7.40−6.90 ppm (m, aromatic porton 3H and imidazol proton 3H), 5.00−4.85 ppm (m, methin proton 2H), 2.70−2.15 ppm (m, methin proton 1H), 1.55−1.05 ppm (m, terminal methyl 3H+3H+3H+3H+3H).

SYNTHETIC EXAMPLE 5

Synthesis of ethyl 3-(2,4-dichlorophenyl)-3-methylthio-2-(1-imidazolyl)-propionate (i.e., Compound No. 73)

A 6.8 g (0.1 mol) amount of sodium ethylate was suspended in 200 ml of diethyl ether and, then, 5.28 g (0.11 mol) of methanethiol was bubbled into the mixture. The mixture was stirred at room temeprature for one hour. After 31.1 g (0.1 mol) of ethyl 3-(2,4-dichlorophenyl)-2-(1-imidazolyl)cinnamate was added, in a limited amount, at room temperature for 18 hours. After the reaction, 100 ml of water was added to the reaction mixture and, then, the mixture was thoroughly mixed. The mixture was allowed to separate into the two phases. The aqueous phase was extracted, twice, with 50 ml of diethyl ether and the combined ether phases were washed with water. The resultant ether extract was dried over anhydrous magnesium sulfate and the solvent was distilled off in vacuo.

The resultant residue was subjected to silica-gel column chromatography and eluted with a 1:1 mixture of ethyl acetate and n-hexane. The desired product was obtained in the form of a pale yellow oil. The yield was 18.3 g (50.9%).

The analytical results are as follows:

NMR: (CDCl$_3$, tetramethyl silane inner standard)

7.50–6.82 ppm (m, aromatic proton 3H and imidazole proton 3H), 5.20–5.05 ppm (m,

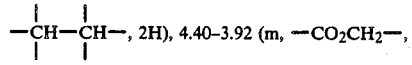

—CH—CH—, 2H), 4.40–3.92 (m, —CO$_2$CH$_2$—,
2H), 2.05 ppm (s, SCH$_3$ of one diastereomer 3H), 1.85 ppm (s, SCH$_3$ of the other diastereomer 3H), 1.45–1.05 ppm (m, —CO$_2$—CH$_2$CH$_3$ 3H)

SYNTHETIC EXAMPLE 6

Synthesis of n-propyl 3-(2,4-dichlorophenyl)-3-methylthio-2-(1-imidazolyl)-propionate (i.e., Compound No. 74)

A 4.8 g (0.1 mol) amount of methanethiol was bubbled into 100 ml of propanol at room temperature and, then, 8.5 g (0.1 mol) of piperidine was added thereto. Thereafter, 32.5 g (0.1 mol) of n-propyl 3-(2,4-dichlorophenyl)-2-(1-imidazolyl)cinnamate was added thereto and the mixture was heated at a boiling point of the solvent for 24 hours. After cooling to room temperature, the reaction mixture was added to a large amount of water and the mixture was extracted, three times, with 100 ml of diethyl ether. The extract was dried over anhydrous magnesium sulfate. The solvent was distilled off in vacuo. The residue was subjected to silica-gel column chromatography and eluted with a 1:1 mixture of n-hexane and ethyl acetate. Thus, the desired product was obtained at a yield of 17.9 g (48%).

NMR (CDCl$_3$, tetramethyl silane inner standard)

7.50-6.85 ppm (m, aromatic proton 3H and imidazole proton 3H), 5.10-4.95 ppm (m, —CH—CH— 2H), 4.30-3.95 ppm (m, n-propyl ester 2H), 2.05 ppm (s, SCH$_3$ of one diastereomer, 3H), 1.85 ppm (s, SCH$_3$ of the other diastereomer, 3H), 1.80-1.30 ppm (m, n-propylester 2H), 1.15-0.85 ppm (m, n-propyl ester 3H)

Various propionate derivatives were prepared in the same manner as mentioned above. The results are shown in the following Table 1, wherein, in the column $R^4$, A represents imidazol-1-yl and B represents triazol-1-yl.

TABLE 1

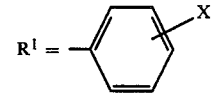

TABLE 1-continued

| Compound No. | $R^1 = $ ⌬—X   X | $R^3 = -SR'$   R' | $R^2$ | $R^4$ | NMR |
|---|---|---|---|---|---|
| 3 | " | —C$_3$H$_7$—i | " | " | 1.0–1.5(m, 6H, —SCH(C$\underline{H}_3$)$_2$), 2.1–3.4(m, 1H, —S—C$\underline{H}$(CH$_3$)$_2$), 3.70, 3.80(s, 3H, —CO$_2$C$\underline{H}_3$), 4.8–5.2 (m, 2H, —S—C$\underline{H}$—C$\underline{H}$—N⟨), 6.6–7.6(m, 6H, aromatic, imidazolyl) |
| 4 | " | —CH$_2$CH=CH$_2$ | " | " | 2.8–3.5(m, 2H, —S—C$\underline{H}_2$—CH=CH$_2$), 3.70, 3.80(s, 3H, —CO$_2$C$\underline{H}_3$), 4.7–5.4(m, 2H, —S—C$\underline{H}$—C$\underline{H}$—N⟨), 6.6–7.7(m, 6H, aromatic, imidazolyl) |
| 5 | " | —C$_4$H$_9$—n | " | " | 0.6–1.9(m, 7H, —S—CH$_2$—C$_3\underline{H}_7$—n), 2.1–2.7(m, 2H, —S—C$\underline{H}_2$—C$_3$H$_7$—n), 3.70, 3.80(s, 3H, —CO$_2$C$\underline{H}_3$), 4.9–5.2(m, 2H, —S—C$\underline{H}$—C$\underline{H}$—N⟨), 6.7–7.6 (m, 6H, aromatic, imidazolyl) |
| 6 | " | ⌬—H (cyclopentyl) | " | " | 0.8–2.3(m, 8H, —SCH(C$\underline{H}_2$)$_4$), 2.3–3.4(m, 1H, —SC$\underline{H}$(CH$_2$)$_4$), 3.70, 3.80(s, 3H, —CO$_2$C$\underline{H}_3$), 4.8–5.3(m, 2H, —S—C$\underline{H}$—C$\underline{H}$—N⟨), 6.7–7.5(m, 6H, aromatic, imidazolyl) |
| 7 | " | —CH$_2$—⌬—Cl | " | " | 2.9–4.2(m, 5H, —S—C$\underline{H}_2$—C$_6$H$_4$—P—Cl, —CO$_2$C$\underline{H}_3$), 4.6–5.5(m, 2H, —S—C$\underline{H}$—C$\underline{H}$—N⟨), 6.5–7.7(m, 10H, aromatic, imidazolyl) |
| 8 | " | —C$_2$H$_5$ | —C$_2$H$_5$ | " | 1.0–1.5(m, 6H, —SCH$_2$—C$\underline{H}_3$, —CO$_2$CH$_2$—C$\underline{H}_3$), 2.1–2.8 (m, 2H, —S—C$\underline{H}_2$—CH$_3$), 3.9–4.5(m, 2H, —CO$_2$C$\underline{H}_2$—), 4.9–5.2(m, 2H, —S—C$\underline{H}$—C$\underline{H}$—N⟨), 6.8–7.6(m, 6H, aromatic, imidazolyl) |
| 9 | " | —C$_3$H$_7$—n | " | " | 0.7–2.9(m, 10H, —S—C$_3$H$_7$—n, —CO$_2$CH$_2$C$\underline{H}_3$), 3.9–4.5 (m, 2H, —CO$_2$C$\underline{H}_2$—), 4.8–5.2(m, 2H, —S—C$\underline{H}$—C$\underline{H}$—N⟨), 6.7–7.8(m, 6H, aromatic, imidazolyl) |
| 10 | " | —C$_3$H$_7$—i | " | " | 1.0–1.7(m, 9H, —SCH(C$\underline{H}_3$)$_2$, —CO$_2$CH$_2$C$\underline{H}_3$), 2.2–3.2 (m, 1H, —SC$\underline{H}$(CH$_3$)$_2$), 4.0–4.5(m, 2H, —CO$_2$C$\underline{H}_2$—), 4.8–5.2(m, 2H, —S—C$\underline{H}$—C$\underline{H}$—N⟨), 6.7–7.6(m, 6H, aromatic, imidazolyl) |
| 11 | " | —CH$_2$—CH=CH$_2$ | " | " | 1.0–1.5(m, 3H, —CO$_2$CH$_2$C$\underline{H}_3$), 2.7–3.3(m, 2H, —S—C$\underline{H}_2$—CH=CH$_2$), 3.9–4.6(m, 2H, —CO$_2$C$\underline{H}_2$—), 4.7–6.0(m, 5H, —S—CH$_2$—C$\underline{H}$=C$\underline{H}_2$, —S—C$\underline{H}$—C$\underline{H}$—N), 6.8–7.6(m, 6H, aromatic, imidazolyl) |

TABLE 1-continued

| Compound No. | $R^1 = \text{phenyl-X}$, X | $R^3 = -SR'$, R' | $R^2$ | $R^4$ | NMR |
|---|---|---|---|---|---|
| 12 | " | —C₄H₉—n | " | " | 0.6–2.0(m, 10H, —SCH₂—C₃$\underline{H}$₇—n, —CO₂CH₂C$\underline{H}$₃), 2.0–2.8(m, 2H, —SC$\underline{H}$₂—C₃H₇—n), 3.9–4.6(m, 2H, —CO₂C$\underline{H}$₂—), 4.8–5.3(m, 2H, —C$\underline{H}$—C$\underline{H}$—N⟨), 6.7–7.7(m, 6H, aromatic, imidazolyl) |
| 13 | " | —C₄H₉—i | " | " | 0.7–2.6(m, 12H, —S—C₄$\underline{H}$₉—i, —CO₂CH₂C$\underline{H}$₃), 3.9–4.5(m, 2H, —CO₂C$\underline{H}$₂—), 4.8–5.2(m, 2H, —S—C$\underline{H}$—C$\underline{H}$—N⟨), 6.8–7.6(m, 6H, aromatic, imidazolyl) |
| 14 | " | cyclopentyl | C₂H₅ | " | 1.0–3.2(m, 12H, —S—CH(C$\underline{H}$₂)₄, —CO₂CH₂—C$\underline{H}$₃), 3.9–4.6(m, 2H, —CO₂C$\underline{H}$₂—), 4.8–5.2(m, 2H, —S—C$\underline{H}$—C$\underline{H}$—N⟨), 6.7–7.6(m, 6H, aromatic, imidazolyl) |
| 15 | " | phenyl | " | " | 0.9–1.6(m, 3H, —CO₂CH₂C$\underline{H}$₃), 3.9–4.5(m, 2H, CO₂C$\underline{H}$₂—), 5.1–5.5(broad, 2H, —S$\underline{H}$—C$\underline{H}$—C$\underline{H}$—N⟨), 6.6–7.6(m, 11H, aromatic, imidazolyl) |
| 16 | " | —C₆H₄—Cl | " | " | 1.0–1.6(m, 3H, —CO₂CH₂C$\underline{H}$₃), 4.0–4.6(m, 2H, CO₂C$\underline{H}$₂—), 5.1–5.3(broad, 2H, —S—C$\underline{H}$—C$\underline{H}$—N⟨), 6.8–7.7(m, 10H, aromatic, imidazolyl) |
| 17 | " | —CH₂—C₆H₄—Cl | " | " | 1.0–1.5(m, 3H, —CO₂CH₂C$\underline{H}$₃), 3.3–4.5(m, 4H, —S—C$\underline{H}$₂—C₆H₄—P—Cl—, —CO₂C$\underline{H}$₂—), 4.8–5.2(m, 2H, —S—C$\underline{H}$—C$\underline{H}$—N⟨), 6.8–7.7(m, 10H, aromatic, imidazolyl) |
| 18 | " | —C₂H₅ | —C₃H₇—i | " | 0.5–1.6(m, 9H, —SCH₂C$\underline{H}$₃, —CO₂CH(C$\underline{H}$₃)₂), 2.0–2.8(m, 2H, —SC$\underline{H}$₂CH₃), 4.5–5.5(m, 3H, —CO₂C$\underline{H}$—, —S—C$\underline{H}$—C$\underline{H}$—N⟨), 6.6–7.7(m, 6H, aromatic, imidazolyl) |
| 19 | " | —C₃H₇—n | " | " | 0.6–1.9(m, 11H, —SCH₂—C₂$\underline{H}$₅, —CO₂CH(C$\underline{H}$₃)₂), 2.0–2.7(m, 2H, —SC$\underline{H}$₂—C₂H₅), 4.5–5.5(m, 3H, —CO₂C$\underline{H}$—, —S—C$\underline{H}$—C$\underline{H}$—N⟨), 6.6–7.6(m, 6H, aromatic, imidazolyl) |
| 20 | " | —C₃H₇—i | " | " | 0.5–1.8(m, 12H, —SCH(C$\underline{H}$₃)₂, —CO₃CH(C$\underline{H}$₃)₂), 2.0–3.2(m, 1H, —SC$\underline{H}$(CH₃)₂), 4.4–5.4(m, 3H, —CO₂C$\underline{H}$—, —SC$\underline{H}$—C$\underline{H}$—N⟨), 6.6–7.7(m, 6H, aromatic, imidazolyl) |

TABLE 1-continued

| Compound No. | $R^1 =$ ⟨phenyl⟩—X  X | $R^3 = -SR'$  R' | $R^2$ | $R^4$ | NMR |
|---|---|---|---|---|---|
| 21 | " | —C$_4$H$_9$—n | " | " | 0.5–1.8(m, 13H, —SCH$_2$—C$_3$$\underline{H}_7$—n, —CO$_2$CH(C$\underline{H}_3$)$_2$), 2.0–2.7(m, 2H, —SC$\underline{H}_2$—C$_3$H$_7$—n), 4.5–5.4(m, 3H, —CO$_2$C$\underline{H}$—, SC$\underline{H}$—C$\underline{H}$—N⟨ ), 6.6–7.6(m, 6H, aromatic, imidazolyl) |
| 22 | " | —C$_4$H$_9$—i | " | " | 0.5–2.9(m, 15H, —S—C$_4$$\underline{H}_9$—i, —CO$_2$CH(C$\underline{H}_3$)$_2$), 4.5–5.4(m, 3H, —CO$_2$C$\underline{H}$—, —SC$\underline{H}$—C$\underline{H}$—N⟨ ), 6.5–7.8(m, 6H, aromatic, imidazolyl) |
| 23 | " | —C$_2$H$_5$ | —C$_3$H$_7$—n | " | 0.4–2.8(m, 10H, —SC$_2$$\underline{H}_5$, —CO$_2$CH$_2$—C$_2$$\underline{H}_5$), 3.8–4.4(m, 2H, —CO$_2$C$\underline{H}_2$—), 4.8–5.1(m, 2H, —S—C$\underline{H}$—C$\underline{H}$—N⟨ ), 6.7–7.5(m, 6H, aromatic, imidazolyl) |
| 24 | " | " | —C$_4$H$_9$—t | " | 0.9–1.7(m, 12H, —SCH$_2$C$\underline{H}_3$, —CO$_2$C$_4$$\underline{H}_9$—t), 2.0–2.7(m, 2H, —SC$\underline{H}_2$—CH$_3$), 4.8–5.1(m, 2H, —S—C$\underline{H}$—C$\underline{H}$—N⟨ ), 6.7–7.6(m, 6H, aromatic, imidazolyl) |
| 25 | " | —C$_3$H$_7$—i | " | " | 1.0–1.7(m, 15H, —SCH(C$\underline{H}_3$)$_2$, —CO$_2$C$_4$$\underline{H}_9$—t), 2.0–3.0(m, 1H, —S—C$\underline{H}$(CH$_3$)$_2$), 4.7–5.2(m, 2H, —S—C$\underline{H}$—C$\underline{H}$—N⟨ ), 6.7–7.5(m, 6H, aromatic, imidazolyl) |
| 26 | " | —C$_2$H$_5$ | —C$_4$H$_9$—n | " | 0.5–2.8(m, 12H, —SC$_2$$\underline{H}_5$, —CO$_2$CH$_2$—C$_3$$\underline{H}_7$—n), 3.9–4.6(m, 2H, —CO$_2$C$\underline{H}_2$—), 4.9–5.2(m, 2H, —S—C$\underline{H}$—C$\underline{H}$—N⟨ ), 6.7–7.6(m, 6H, aromatic, imidazolyl) |
| 27 | " | —C$_3$H$_7$—n | " | " | 0.6–2.0(m, 12H, —CO$_2$CH$_2$—C$_3$$\underline{H}_7$—n, —S—CH$_2$—C$_2$$\underline{H}_5$), 2.0–2.7(m, 2H, —S—C$\underline{H}_2$—C$_2$H$_5$), 3.8–4.5(m, 2H, —CO$_2$C$\underline{H}_2$—), 4.8–5.3(m, 2H, —S—C$\underline{H}$—C$\underline{H}$—N⟨ ), 6.7–7.6(m, 6H, aromatic, imidazolyl) |
| 28 | " | —C$_3$H$_7$—i | " | " | 0.7–2.0(m, 13H, —SCH(C$\underline{H}_3$)$_2$, —CO$_2$CH$_2$—C$_3$$\underline{H}_7$—n), 2.2–3.3(m, 1H, —SC$\underline{H}$(CH$_3$)$_2$), 3.9–4.5(m, 2H, —CO$_2$C$\underline{H}_2$—), 4.9–5.2(m, 2H, —S—C$\underline{H}$—C$\underline{H}$—N⟨ ), 6.7–7.5(m, 6H, aromatic, imidazolyl) |
| 29 | " | —CH$_2$CH=CH$_2$ | " | " | 0.6–2.3(m, 7H, —CO$_2$CH$_2$—C$_3$$\underline{H}_7$—n), 2.6–3.2(m, 2H, —S—C$\underline{H}_2$—CH=CH$_2$), 3.8–4.5(m, 2H, —CO$_2$C$\underline{H}_2$—), 4.6–6.0(m, 5H, —S—CH$_2$—C$\underline{H}$=C$\underline{H}_2$, —S—C$\underline{H}$—C$\underline{H}$—N⟨ ), 6.6–7.6(m, 6H, aromatic, imidazolyl) |

TABLE 1-continued $R^1 = $ phenyl-X ; $R^3 = -SR'$

| Compound No. | X | R' | $R^2$ | $R^4$ | NMR |
|---|---|---|---|---|---|
| 30 | " | cyclopentyl (-CH with (CH$_2$)$_4$ ring) | " | " | 0.5–3.2(m, 16H, $-CO_2CH_2-C_3H_7-n$, $-S-C\underline{H}(CH_2)_4$), 3.8–4.5(m, 2H, $-CO_2C\underline{H}_2-$), 4.8–5.1(m, 2H, $-S-C\underline{H}-C\underline{H}-N\diagup\diagdown$), 6.6–7.6(m, 6H, aromatic, imidazolyl) |
| 31 | 4-Cl | $-C_2H_5$ | $-C_2H_5$ | " | 0.6–1.5(m, 6H, $-SCH_2C\underline{H}_3$, $-CO_2CH_2C\underline{H}_3$), 2.1–2.6(m, 2H, $-SC\underline{H}_2-CH_3$), 4.0–5.0(m, 4H, $-CO_2C\underline{H}_2-$, $-S-C\underline{H}-C\underline{H}-N\diagup\diagdown$), 6.5–7.7(m, 7H, aromatic, imidazolyl) |
| 32 | " | $-C_3H_7-n$ | " | " | 0.6–1.8(m, 8H, $-SCH_2-C_2\underline{H}_5$, $-CO_2CH_2-C\underline{H}_3$), 1.9–2.5(m, 2H, $-SC\underline{H}_2-C_2H_5$), 3.8–5.0(m, 4H, $-CO_2C\underline{H}_2-$, $-S-C\underline{H}-C\underline{H}-N\diagup\diagdown$), 6.5–7.6(m, 7H, aromatic, imidazolyl) |
| 33 | " | $-C_3H_7-i$ | " | " | 0.6–1.7(m, 9H, $-SCH(C\underline{H}_3)_2$, $-CO_2CH_2-C\underline{H}_3$), 2.0–3.1(m, 1H, $-SC\underline{H}(CH_3)_2$), 3.7–5.0(m, 4H, $-CO_2C\underline{H}_2-$, $-SC\underline{H}-C\underline{H}-N\diagup\diagdown$), 6.5–7.7(m, 7H, aromatic, imidazolyl) |
| 34 | 2,4-(CH$_3$)$_2$ | $-C_2H_5$ | " | " | 0.7–1.4(m, 6H, $-SCH_2C\underline{H}_3$, $-CO_2CH_2-C\underline{H}_3$), 1.7–2.7(m, 8H, $-SC\underline{H}_2CH_3$, $-C\underline{H}_3$(aromatic)×2), 3.6–5.1(m, 4H, $-CO_2C\underline{H}_2-$, $-SC\underline{H}-C\underline{H}-N\diagup\diagdown$), 6.5–7.8(m, 6H, aromatic imidazolyl) |
| 35 | 3,4-Cl$_2$ | " | " | " | 0.9–1.5(m, 6H, $-SCH_2C\underline{H}_3$, $-CO_2CH_2C\underline{H}_3$), 1.8–2.5(m, 2H, $-SC\underline{H}_2CH_3$), 3.8–4.5(m, 2H, $-CO_2C\underline{H}_2-$), 4.6–5.0(m, 2H, $-S-C\underline{H}-C\underline{H}-N\diagup\diagdown$), 6.7–7.5(m, 6H, aromatic, imidazolyl) |
| 36 | " | $-C_3H_7-n$ | " | " | 0.6–1.9(m, 8H, $-S-CH_2-C_2\underline{H}_5$, $-CO_2CH_2C\underline{H}_3$), 2.0–2.6(m, 2H, $-SC\underline{H}_2CH_3$), 3.8–4.5(m, 2H, $-CO_2C\underline{H}_2-$), 4.6–5.0(m, 2H, $-S-C\underline{H}-C\underline{H}-N\diagup\diagdown$), 6.8–7.7(m, 6H, aromatic, imidazolyl) |
| 37 | " | $-C_3H_7-i$ | " | " | 0.9–1.5(m, 9H, $-S-CH-(C\underline{H}_3)_2$, $-CO_2CH_2C\underline{H}_3$), 2.1–2.9(m, 1H, $-S-C\underline{H}(CH_3)_2$, 3.8–5.0(m, 4H, $-CO_2C\underline{H}_2-$, $-S-C\underline{H}-C\underline{H}-N\diagup\diagdown$), 6.7–7.6(m, 6H, aromatic, imidazolyl) |
| 38 | 3,4-(OCH$_3$)$_2$ | $-C_2H_5$ | " | " | 0.7–1.9(m, 6H, $-SCH_2-C\underline{H}_3$, $-CO_2CH_2C\underline{H}_3$), 2.0–2.6(m, 2H, $-SC\underline{H}_2CH_3$), 3.4–5.1(m, 10H, $-OC\underline{H}_3$(aromatic)×2, $-CO_2C\underline{H}_2-$, $-SC\underline{H}-C\underline{H}-N\diagup\diagdown$), 6.4–7.9(m, 6H, aromatic, imidazolyl) |

TABLE 1-continued

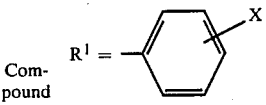

| Compound No. | X | R³ = —SR' R' | R² | R⁴ | NMR |
|---|---|---|---|---|---|
| 39 | " | —C$_3$H$_7$—n | " | " | 0.6–1.9(m, 8H, —SCH$_2$—C$_2$H$_5$, —CO$_2$CH$_2$CH$_3$), 1.9–2.8 (m, 2H, —SCH$_2$—C$_2$H$_5$), 3.5–5.0(m, 10H, —OCH$_2$ (aromatic)×2, —CO$_2$CH$_2$—, —SCH—CH—N<), 6.4–7.8(m, 6H, aromatic, imidazolyl) |
| 40 | " | —C$_3$H$_7$—i | " | " | 0.9–1.6(m, 9H, —SCH(CH$_3$)$_2$, —CO$_2$CH$_2$CH$_3$), 2.2–3.1 (m, 1H, SCH(CH$_3$)$_2$), 3.5–4.9(m, 10H, OCH$_3$ (aromatic)×2, —CO$_2$CH$_2$—, —SCH—CH—N<), 6.5–7.6(m, 6H, aromatic, imidazolyl) |
| 41 | 2-Cl, 6-F | C$_2$H$_5$ | " | " | 0.8–1.6(m, 6H, —SCH$_2$CH$_3$, —CO$_2$CH$_2$CH$_3$), 2.4–3.0 (m, 2H, —SCH$_2$CH$_3$), 3.8–4.5(m, 2H, —CO$_2$CH$_2$—), 5.0–5.4 (broad, 2H, —S—CH—CH—N<), 6.6–7.5(m, 6H, aromatic, imidazolyl) |
| 42 | " | —C$_3$H$_7$—i | " | " | 0.8–1.6(m, 9H, —SCH(CH$_3$)$_2$, —CO$_2$CH$_2$CH$_3$), 2.7–3.4 (m, 1H, —SCH(CH$_3$)$_2$, 3.7–4.5(m, 2H, —CO$_2$CH$_2$—), 4.8–5.3(m, 2H, —S—CH—CH—N<), 6.7–7.5(m, 6H, aromatic, imidazolyl) |
| 43 | 3,4(—OCH$_2$O—) | " | " | " | 0.9–1.6(m, 9H, —SCH(CH$_3$)$_2$, —CO$_2$CH$_2$CH$_3$), 2.0–3.0 (m, 1H, —SCH(CH$_3$)$_2$), 3.8–5.0(m, 4H, —CO$_2$CH$_2$—, —S—CH—CH—N<), 5.8–6.1(m, 2H, —O—CH$_2$—O—), 6.5–7.8(m, 6H, aromatic, imidazolyl) |
| 44 | 2,4-Cl$_2$ | —C$_2$H$_5$ | —CH$_3$ | B | 1.0–1.5(m, 3H, —S—CH$_2$—CH$_3$), 2.0–3.0(m, 2H, —S—CH$_2$—CH$_3$), 3.75, 3.85(s, 3H, —CO$_2$CH$_3$), 4.9–5.7 (m, 2H, —S—CH—CH—N<), 7.0–8.5(m, 5H, aromatic, triazolyl) |
| 45 | " | —C$_3$H$_7$—n | " | " | 0.7–2.0(m, 5H, —S—CH$_2$—C$_2$H$_5$), 2.1–2.7(m, 2H, —S—CH$_2$—C$_2$H$_5$), 3.70, 3.80(s, 3H, —CO$_2$CH$_3$), 5.0–5.8 (m, 2H, —S—CH—CH—N<), 7.0–8.5(m, 5H, aromatic, triazolyl) |
| 46 | " | —C$_3$H$_7$—i | " | " | 1.0–9.5(m, 6H, —SCH(CH$_3$)), 2.2–3.3(m, 1H, —SCH(CH$_3$)$_2$), 3.75–3.80(s, 3H, —CO$_2$CH$_3$), 5.1–5.8(m, 2H, —S—CH—CH—N<), 7.0–8.6(m, 5H, aromatic, triazolyl) |
| 47 | " | —CH$_2$—CH=CH$_2$ | " | " | 2.7–3.4(m, 2H, —S—CH$_2$—CH=CH$_2$), 3.70, 3.75(s, 3H, —CO$_2$CH$_3$), 4.7–6.0(m, 5H, —S—CH$_2$—CH=CH$_2$, —S—CH—CH—N<), 7.0–8.5(m, 5H, aromatic, triazolyl) |

TABLE 1-continued

| Compound No. | $R^1 =$ X | $R^3 = -SR'$ R' | $R^2$ | $R^4$ | NMR |
|---|---|---|---|---|---|
| 48 | " | $-C_2H_5$ | $-C_2H_5$ | " | 1.0–1.6(m, 6H, $-S-CH_2-C\underline{H_3}$, $-CO_2CH_2-C\underline{H_3}$), 2.0–2.8(m, 2H, $-S-C\underline{H_2}-CH_3$), 3.9–4.6(m, 2H, $-CO_2C\underline{H_2}-$), 4.9–5.7(m, 2H, $-S-C\underline{H}-C\underline{H}-N\diagup_\diagdown$), 7.0–8.5(m, 5H, aromatic, triazolyl) |
| 49 | " | $-C_3H_7-i$ | " | " | 1.1–1.6(m, 9H, $-S-CH(C\underline{H_3})_2$, $-CO_2CH_2C\underline{H_3}$), 2.0–3.2(m, 1H, $-SC\underline{H}(CH_3)_2$), 4.0–4.6(m, 2H, $-CO_2C\underline{H_2}-$), 4.9–5.7(m, 2H, $-S-C\underline{H}-C\underline{H}-N\diagup_\diagdown$), 7.0–8.5(m, 5H, aromatic, triazolyl) |
| 50 | 2-Cl, 6-F | $-C_2H_5$ | " | " | 0.8–1.5(m, 6H, $-SCH_2-C\underline{H_3}$, $-CO_2CH_2C\underline{H_3}$), 2.1–3.0(m, 2H, $-S-C\underline{H_2}-CH_3$), 3.8–4.5(m, 2H, $-CO_2C\underline{H_2}-$), 5.0–5.8(m, 2H, $-S-C\underline{H}-C\underline{H}-N\diagup_\diagdown$), 6.7–8.4(m, 5H, aromatic, triazolyl) |
| 51 | " | $-C_3H_7-i$ | " | " | 0.8–1.5(m, 9H, $-SCH(C\underline{H_3})_2$, $-CO_2CH_2C\underline{H_3}$), 2.2–3.3(m, 1H, $-SC\underline{H}(CH_3)_2$), 3.8–4.5(m, 2H, $-CO_2C\underline{H_2}-$), 5.0–5.8(m, 2H, $-S-C\underline{H}-C\underline{H}-N\diagup_\diagdown$), 6.7–8.4(m, 5H, aromatic, triazolyl) |
| 52 | 2,4-Cl$_2$ | $-C_4H_9-t$ | $-C_2H_5$ | A | 1.1–1.5(m, 12H, $-S-C_4\underline{H_9}$, $-CO_2CH_2C\underline{H_3}$), 3.9–4.5(m, 2H, $-CO_2C\underline{H_2}-$), 4.6–5.3(m, 2H, $-S-C\underline{H}-C\underline{H}-N\diagup_\diagdown$), 6.8–7.5(m, 6H, aromatic, imidazolyl) |
| 53 | " | " | $-C_3H_7-n$ | " | 0.7–2.0(m, 14H, $-S-C_4\underline{H_9}$, $-CO_2CH_2-C_2\underline{H_5}$), 3.8–4.4(m, 2H, $-CO_2C\underline{H_2}-$), 4.7–5.3(m, 2H, $-S-C\underline{H}-C\underline{H}-N\diagup_\diagdown$), 6.7–7.6(m, 6H, aromatic, imidazolyl) |
| 54 | " | $-C_3H_7-n$ | " | " | 0.6–2.0(m, 10H, $-SCH_2-C_2\underline{H_5}$, $-CO_2CH_2-C_2\underline{H_5}$), 2.1–2.7(m, 2H, $-S-C\underline{H_2}-CH_5$), 3.9–4.3(m, 2H, $-CO_2C\underline{H_2}-$), 4.8–5.3(m, 2H, $-S-C\underline{H}-C\underline{H}-N\diagup_\diagdown$), 6.6–7.7(m, 6H, aromatic, imidazolyl) |
| 55 | " | $-C_3H_7-i$ | " | " | 0.7–2.0(m, 11H, $-SCH(C\underline{H_3})_2$, $-CO_2CH_2-C_2\underline{H_5}$), 2.2–3.2(m, 1H, $-SC\underline{H}(CH_3)_2$), 3.9–4.3(m, 2H, $-CO_2C\underline{H_2}-$), 4.8–5.3(m, 2H, $-S-C\underline{H}-C\underline{H}-N\diagup_\diagdown$), 6.7–7.5(m, 6H, aromatic, imidazolyl) |
| 56 | " | $-C_4H_9-n$ | " | " | 0.6–2.0(m, 12H, $-SCH_2-C_3\underline{H_7}-n$, $-CO_2CH_2-C_2\underline{H_5}$), 2.1–2.7(m, 2H, $-S-C\underline{H_2}-C_3H_7-n$), 3.9–4.3(m, 2H, $-CO_2C\underline{H_2}-$), 4.8–5.3(m, 2H, $-S-C\underline{H}-C\underline{H}-N\diagup_\diagdown$), 6.6–7.6(m, 6H, aromatic, imidazolyl) |

TABLE 1-continued

| Compound No. | $R^1 = $ [phenyl]—X, X | $R^3 = -SR'$, R' | $R^2$ | $R^4$ | NMR |
|---|---|---|---|---|---|
| 57 | " | $-C_4H_9-i$ | " | " | 0.7–2.6(m, 14H, $-S-C_4\underline{H}_9-i$, $-CO_2CH_2-C_2\underline{H}_5$), 3.9–4.3(m, 2H, $-CO_2C\underline{H}_2-$), 4.8–5.3(m, 2H, $-S-C\underline{H}-C\underline{H}-N\diagup\diagdown$), 6.6–7.5(m, 6H, aromatic, imidazolyl) |
| 58 | " | $-CH_2CH=CH_2$ | " | " | 0.6–3.2(m, 7H, $-S-C\underline{H}_2-CH=CH_2$, $-CO_2CH_2-C_2\underline{H}_5$), 3.9–4.4(m, 2H, $-CO_2C\underline{H}_2-$), 4.6–6.0(m, 5H, $-S-CH_2-C\underline{H}=C\underline{H}_2$, $-S-C\underline{H}-C\underline{H}-N\diagup\diagdown$), 6.6–7.6(m, 6H, aromatic, imidazolyl) |
| 59 | " | [cyclopentyl]—H | " | " | 0.5–3.2(m, 14H, $-S-CH(C\underline{H}_2)_4$, $-CO_2CH_2-C_2\underline{H}_5$), 3.9–4.5(m, 2H, $-CO_2C\underline{H}_2-$), 4.8–5.2(m, 2H, $-S-C\underline{H}-C\underline{H}-N\diagup\diagdown$), 6.6–7.6(m, 6H, aromatic, imidazolyl) |
| 60 | 4-Cl | $-C_2H_5$ | " | " | 0.7–2.0(m, 8H, $-S-CH_2C\underline{H}_3$, $-CO_2CH_2-C_2\underline{H}_5$), 2.1–2.7(m, 2H, $-S-C\underline{H}_2-CH_3$), 4.0–5.0(m, 4H, $-CO_2C\underline{H}_2-$, $-SC\underline{H}-C\underline{H}-N\diagup\diagdown$), 6.5–7.8(m, 7H, aromatic, imidazolyl) |
| 61 | " | $-C_3H_7-n$ | " | " | 0.5–2.0(m, 10H, $-S-CH_2-C_2\underline{H}_5$, $-CO_2CH_2C_2\underline{H}_5$), 2.0–2.8(m, 2H, $-S-C\underline{H}_2-C_2H_5$), 4.0–5.1(m, 4H, $-CO_2C\underline{H}_2-$, $SC\underline{H}-C\underline{H}-N\diagup\diagdown$), 6.6–7.8(m, 7H, aromatic, imidazolyl) |
| 62 | " | $-C_3H_7-i$ | " | " | 0.7–2.0(m, 11H, $-S-CH(C\underline{H}_3)_2$, $-CO_2CH_2C_2\underline{H}_5$), 2.0–3.2(m, 1H, $-SC\underline{H}(CH_3)_2$), 3.8–5.0(m, 4H, $-CO_2C\underline{H}_2-$, $-SC\underline{H}-C\underline{H}-N\diagup\diagdown$), 6.6–7.7(m, 7H, aromatic, imidazolyl) |
| 63 | " | $-C_4H_9-n$ | " | " | 0.5–2.0(m, 12H, $-SCH_2-C_3\underline{H}_7-n$, $-CO_2CH_2C_2\underline{H}_5$), 2.0–2.9(m, 2H, $-SC\underline{H}_2-C_3H_7-n$), 3.8–5.1(m, 4H, $-CO_2C\underline{H}_2-$, $-SC\underline{H}-C\underline{H}-N\diagup\diagdown$), 6.6–7.7(m, 7H, aromatic, imidazolyl) |
| 64 | " | $-C_4H_9-i$ | " | " | 0.5–2.9(m, 14H, $-S-C_4\underline{H}_9-i$, $-CO_2CH_2-C_2\underline{H}_5$), 3.8–5.1(m, 4H, $-CO_2C\underline{H}_2-$, $-SC\underline{H}-C\underline{H}-N\diagup\diagdown$), 6.5–7.8(m, 7H, aromatic, imidazolyl) |
| 65 | " | $-C_4H_9-t$ | " | " | 0.6–2.0(m, 14H, $-S-C_4\underline{H}_9-t$, $-CO_2CH_2-C_2\underline{H}_5$), 4.0–4.9(m, 4H, $-CO_2C\underline{H}_2-$, $-SC\underline{H}-C\underline{H}-N\diagup\diagdown$), 6.6–7.5(m, 7H, aromatic, imidazolyl) |

TABLE 1-continued

| Compound No. | $R^1 = $ 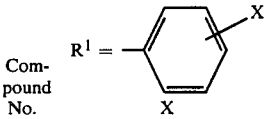 X | $R^3 = -SR'$ R' | $R^2$ | $R^4$ | NMR |
|---|---|---|---|---|---|
| 66 | H | $-C_2H_5$ | $-C_2H_5$ | " | 0.8–1.8(m, 6H, $-SCH_2-C\underline{H}_3$, $-CO_2CH_2-C\underline{H}_3$), 1.9–2.7(m, 2H, $-SC\underline{H}_2-CH_3$), 3.7–4.6(m, 3H, $-CO_2C\underline{H}_2-$, $-SC\underline{H}-CH-N\diagup\diagdown$), 4.7–5.1(m, 1H, $-SCH-C\underline{H}-N\diagup\diagdown$), 6.7–7.9(m, 8H, aromatic, imidazolyl) |
| 67 | " | $-C_3H_7-i$ | " | " | 0.8–1.7(m, 9H, $-SCH(C\underline{H}_3)_2$, $-CO_2CH_2-C\underline{H}_3$), 2.0–3.1 (m, 1H, $-SC\underline{H}(CH_3)_2$), 3.7–5.1(m, 4H, $-CO_2C\underline{H}_2-$, $-SC\underline{H}-C\underline{H}-N\diagup\diagdown$), 6.6–7.9(m, 8H, aromatic, imidazolyl) |
| 68 | 3-Cl | $-C_2H_5$ | $-C_3H_7-n$ | " | 0.5–2.8(m, 10H, $-SC_2\underline{H}_5$, $-CO_2CH_2-C_2\underline{H}_5$), 3.8–4.6(m, 3H, $-CO_2C\underline{H}_2-$, $-SC\underline{H}-CH-N$), 4.7–5.1(m, 1H, $-SCH-C\underline{H}-N\diagup\diagdown$), 6.8–7.8(m, 7H, aromatic, imidazolyl) |
| 69 | 4-F | " | " | " | 0.6–2.6(m, 10H, $-S-C_2\underline{H}_5$, $-CO_2CH_2-C_2\underline{H}_5$), 3.7–4.6 (m, 3H, $-CO_2C\underline{H}_2-$, $-SC\underline{H}-CH-N\diagup\diagdown$), 4.7–5.1(m, 1H, $-SCH-C\underline{H}-N\diagup\diagdown$), 6.8–7.7(m, 7H, aromatic, imidazolyl) |
| 70 | " | $-C_3H_7-i$ | " | " | 0.5–3.2(m, 11H, $-S-C_3\underline{H}_7-i$, $-CO_2CH_2-C_2\underline{H}_5$), 3.8–5.0(m, 4H, $-CO_2C\underline{H}_2-$, $-SC\underline{H}-C\underline{H}-N\diagup\diagdown$), 6.5–7.8(m, 7H, aromatic, imidazolyl) |
| 71 | " | $-C_4H_9-t$ | " | " | 0.6–2.0(m, 14H, $-S-C_4\underline{H}_9-t$, $-CO_2CH_2-C_2\underline{H}_5$), 3.7–4.9(m, 4H, $-S-C\underline{H}-C\underline{H}-N\diagup\diagdown$), 6.6–7.6(m, 7H, aromatic, imidazolyl) |
| 72 | 2,4-Cl$_2$ | $-CH_3$ | $-CH_3$ | " | 1.88, 2.08(s, 3H, $-SC\underline{H}_3$), 3.58, 3.72(s, 3H, $-CO_2C\underline{H}_3$), 4.9–5.05(m, 2H $\diagdown C\underline{H}C\underline{H}\diagup$), 6.75–7.4(m, 6H, aromatic, imidazolyl) |
| 73 | " | " | $-C_2H_5$ | " | 1.05–1.45(m, 3H, $-CO_2CH_2C\underline{H}_3$), 1.85, 2.05(S, 3H, $-SC\underline{H}_3$), 3.92–4.40(m, 2H, $-CO_2C\underline{H}_2CH_3$), 5.05–5.20 (m, 2H, $-C\underline{H}-C\underline{H}-$), 6.82–7.50(m, 6H, aromatic, imidazolyl) |
| 74 | " | " | $-C_3H_7-n$ | " | 0.85–1.15(m, 3H, $-CO_2CH_2CH_2C\underline{H}_3$), 4.95–5.10(m, 2H, $\diagdown C\underline{H}-C\underline{H}\diagup$), 6.85–7.50(m, 6H, aromatic, imidazolyl) |

The typical metal complexes of the propionate derivatives are as shown in Table 2, wherein n represents the The typical synthesis of these compounds are shown below.

TABLE 2

$R^1 = $ —phenyl—X, $R^3 = -SR'$

| Compound No. | X | R' | $R^2$ | $R^4$ | Metal salt | n | m.p. (°C.) |
|---|---|---|---|---|---|---|---|
| 75 | 2,4-Cl$_2$ | CH$_3$ | CH$_3$ | A | CuCl$_2$ | 2 | 82–84 |
| 76 | 2,4-Cl$_2$ | CH$_3$ | C$_2$H$_5$ | A | CuSO$_4$ | 2 | 163–165 |
| 77 | 2,4-Cl$_2$ | CH$_3$ | C$_2$H$_5$ | A | CoBr$_2$ | 4 | 66–69 |
| 78 | 2,4-Cl$_2$ | CH$_3$ | C$_2$H$_5$ | A | CuCl$_2$ | 2 | 71.5–72.5 |
| 79 | 2,4-Cl$_2$ | C$_2$H$_5$ | C$_2$H$_5$ | A | CuCl$_2$ | 2 | 65–66 |
| 80 | 2,4-Cl$_2$ | CH$_3$ | n-C$_3$H$_7$ | A | CuCl$_2$ | 2 | 71.5–73.5 |
| 81 | 4-Cl | CH$_3$ | C$_2$H$_5$ | A | CuCl$_2$ | 2 | |
| 82 | 2,4-Cl$_2$ | CH$_3$ | C$_2$H$_5$ | A | ZnCl$_2$ | 2 | 76–78 |
| 83 | 2,4-Cl$_2$ | CH$_3$ | CH$_3$ | A | ZnCl$_2$ | 2 | 79–81 |
| 84 | 2,4-Cl$_2$ | C$_2$H$_5$ | t-C$_4$H$_9$ | A | CuCl$_2$ | 2 | 82–84 |
| 85 | 2,4-Cl$_2$ | n-C$_4$H$_9$ | C$_2$H$_5$ | A | CuCl$_2$ | 2 | 75–77 |
| 86 | 2,4-Cl$_2$ | C$_2$H$_5$ | CH$_3$ | A | CuCl$_2$ | 2 | 110–111 |

TABLE 3

| Compound No. | Found (%) | | | Calc. (%) | | |
|---|---|---|---|---|---|---|
| | H | C | N | H | C | N |
| 75 | 3.34 | 38.50 | 6.47 | 3.40 | 40.75 | 6.79 |
| 76 | 3.41 | 40.54 | 6.11 | 3.65 | 41.02 | 6.38 |
| 77 | 3.80 | 42.94 | 6.66 | 3.87 | 43.51 | 6.78 |
| 78 | 3.57 | 40.72 | 6.28 | 3.75 | 42.23 | 6.57 |
| 79 | 3.84 | 41.68 | 6.33 | 4.09 | 43.61 | 6.36 |
| 80 | 3.86 | 40.99 | 6.27 | 4.09 | 43.61 | 6.36 |
| 81 | 4.29 | 45.31 | 6.96 | 4.34 | 45.95 | 7.15 |
| 82 | 3.41 | 40.55 | 6.31 | 3.74 | 42.13 | 6.65 |
| 83 | 3.12 | 38.57 | 6.24 | 3.39 | 40.66 | 6.78 |
| 84 | 4.21 | 43.98 | 5.47 | 4.70 | 46.13 | 5.98 |
| 85 | 4.14 | 43.74 | 5.26 | 4.70 | 46.13 | 5.98 |
| 86 | 3.33 | 40.95 | 6.24 | 3.75 | 42.23 | 6.57 |

SYNTHETIC EXAMPLE 7

Synthesis of Compound No. 75

A 3.3 g amount of methyl 3-(2,4-dichlorophenyl)-2-(1-imidazolyl)-3-methylthiopropionate obtained above (i.e., Compound No. 72) was dissolved in 20 ml of ethanol and a solution of 0.9 g of CuCl.2H$_2$0 dissolved in 10 ml of ethanol was added thereto. The mixture was stirred at room temperature for 5 hours. The precipitated crystal was separated by filtration, followed by vacuum drying. Thus, 3.4 g of the desired methyl 3-(2,4-dichlorophenyl)-2-(1-imidazolyl)-3-methylthiopropionate copper chloride salt was obtained.

The analytical results are as follows:

m.p.: 82°–84° C. Cu content (atomic absorption spectrometry) Found: 7.1%. Calc: 7.38%.

IR: (KBr tablet): 3150, 3000, 2950, 1750, 1590, 1520, 1480, 1100.

SYNTHETIC EXAMPLE 8

Synthesis of Compound No. 76

A 3.5 g amount of ethyl 3-(2,4-dichlorophenyl)-2-(1-imidazolyl)-3-methylthiopropionate obtained above (i.e., Compound No. 73) was dissolved in 10 ml of ethanol and a solution of 1.4 g of CuSO$_4$.5H$_2$O dissolved in 10 ml of ethanol was added thereto. The mixture was stirred at room temperature for 5 hours. The precipitated crystal was separated by filtration, followed by vacuum drying. Thus, 3.9 of the desired ethyl 3-(2,4-dichlorophenyl)-2-(1-imidazolyl)-3-methylthiopropionate copper sulfate salt was obtained.

The analytical data are as follows:
m.p.: 163°–165° C. Copper content Found. 7.5%. Calc. 7.32%.

SYNTHETIC EXAMPLE 9

Synthesis of Compound No. 77

A 3.5 g amount of ethyl 3-(2,4-dichlorophenyl)-2-(1-imidazolyl)-3-methylthiopropionate was obtained above (i.e., Compound No. 73) was dissolved in 20 ml of ethanol and a solution of 1 g of CoBr$_2$.5H$_2$O dissolved in 10 ml of ethanol was dropwise added thereto. The mixture was stirred at room temperature for 5 hours and the mixture was, then, poured into cool water to precipitate the crystal. The resultant crystal was separated by suction filtration, followed by vacuum drying. Thus, the desired ethyl 3-(2,4-dichlorophenyl)-2-(1-imidazolyl)-3-methylthiopropionate cobalt bromide salt was obtained at a yield of 3.9 g.

The analytical data are as follows:
m.p.: 66°–68° C. Cobalt content: Found. 3.3%. Calc. 3.56%.

IR: 3150, 3000, 2950, 1745, 1590, 1520, 1480, 1240, 1110, 1095.

SYNTHETIC EXAMPLE 10

Synthesis of Compound No. 82

A 1.7 g amount of ethyl 3-(2,4-dichlorophenyl)-2-(1-imidazolyl)-3-methylthiopropionate obtained above (i.e., Compound No. 73) was dissolved in 10 ml of ethanol and a solution of 0.4 g of zinc chloride in 10 ml of ethanol was dropwise added at room temperature while stirring. After the dropwise addition, the mixture was stirred at room temperature for 3 hours. After the reaction, 10 ml of cooled water was added thereto. The resultant crystal was recovered by suction filtration, followed by vacuum drying. Thus, the desired ethyl 3-(2,4-dichlorophenyl)-2-(1-imidazolyl)-3-methylthio propionate at a yield of 1.8 g.

The analytical data are as follows:
m.p.: 76°–78° C. Zn content: Found.: 7.1%. Calc.: 7.65%.

IR: 3150, 2980, 1755, 1590, 1520, 1480, 1240, 1100.

The propionate derivatives (I) and the metal complexes thereof (I') are effective for controlling a wide variety of diseases of various agricultural and garden crops. Examples of such diseases and miroorganisms are as follows.

Rice: Blast, Helminthosporium leaf spot, Sheath blight, "Bakanae" disease, Seedling blight Wheat: Leaf rust, Stripe rust, Loose smut, Speckled leaf blotch, Spot blotch, Browning root rot, Powdery mildew, Typhula snow blight Potato: Late blight, Early blight, Black scurf, Scab, Fusarium wilt Maize, Corn: Leaf spot, Eyespot, Smut, Rust Soybean: Downy mildew, Cercospora leaf spot, Leaf spot, Septoria brown spot, Sclerotinia rot, Rust, Purple stain Adzuki bean: Leaf spot, Rust, Leaf spot, Powdery mildew Peanut: Brown leaf spot, Leaf spot, Sclerotinia rot Tobacco: Brown spot, Black shank, Sclerotinia stem-rot Sore shin, Damping-off, Bed rot, Frog-eye, Powdery mildew Sugar beet: Downy mildew, Leaf blight, Cercospora leaf spot, Damping-off Tomato: Gray mold, Leaf mold, Late blight, Stem rot, Early blight, Cercospora leaf mold, Fusarium wilt, Damping-off Eggplant: Gray mold, Verticillium wilt, Brown rot, Black rot, Powdery mildew, Leaf mold, Stem rot Cucurbit: Downy mildew, Phytophthora rot, Gray mold, Sclerotinia rot, Scab, Anthracnose, Gummy stem blight, Fusarium wilt, Powdery mildew, Damping-off Japanese radish: Downy mildew, Yellows, Alternaria leaf spot, Clubroot Chinese cabbage: Downy mildew, Leaf spot, Alternaria leaf spot, Sclerotinia rot, Clubroot Cabbage: Downy mildew, Yellows, Sclerotinia rot, Alternaria leaf spot, Damping-off, Clubroot Onion: Downy mildew, Gray-mold neck rot, Gray mold, Fusarium basal rot, Watery soft rot, Alternaria leaf spot, Black spotted leaf blight, Rust, Phytophthora rot Lettuce: Downy mildew, Gray mold, Leaf spot, Stem rot, Root rot, Bottom rot Spinach: Downy mildew, Leaf spot, Foot rot, Leaf spot, Root rot, Damping-off Strawberry: Gnomonia leaf spot, Gray mold, Fusarium wilt, Powdery mildew, Leaf blight, Leaf spot Chrysanthemum: Rust, Powdery mildew, Leaf blight Cyclamen: Gray mold, Leaf spot Rose: Black spot, Powdery mildew, Botrytis blight Citrus: Pink disease, Blue mold, Penicillium rot, Gray mold, Melanose, Scab, Anthracnose Apple: Rust, Blight, Crown rot, Silver leaf, Brown rot, Alternaria leaf spot, Canker, Blotch, Scab, Ring rot, Sooty blotch, Fly speck, Bitter rot, Powdery mildew Pear: Rust, Canker, Black spot, Scab, Physalospora canker Peach: Canker, Brown rot, Gray mold, Blister canker, Scab, Phomopsis rot, Leaf curl, Anthracnose Grape: Downy mildew, Gray mold, Black rot, Leaf spot, Brown spot, Anthracnose, Ripe rot, Pestalotia disease, Rust, Dead arm, Powdery mildew Persimmon: Canker, Leaf spot, Anthracnose, Cercospora leaf spot, Angular leaf spot, Phoma spot, Black spot, Circular leaf spot, Banana: Leaf spot Pineapple: Heart rot Tea: Brown blight, Net blister blight, Brown round spot, Blister blight, Gray blight, White scab, Anthracnose Formulation Example 1

Powder fungicides having the following compositions were prepared by mixing the ingredients listed below at room temperature.

| Ingredient | Parts by weight |
|---|---|
| Compound listed in Table 1 or 2 | 3 |
| Clay | 40 |
| Talc | 57 |

The powder fungicides thus obtained were evaluated in the Test Examples below.

Formulation Example 2

Wettable powder fungicides having the following compositions were prepared by mixing the ingredients listed below at room temperature.

| Ingredient | Parts by weight |
|---|---|
| Compound listed in Table 1 or 2 | 25 |
| Polyoxyethylene alkylarylether | 9 |
| White carbon | 16 |
| Talc | 50 |

Formulation Example 3

Emulsion fungicides having the following compositions were prepared by mixing the ingredients listed below at room temperature.

| Ingredient | Parts by weight in 100 ml |
|---|---|
| Compound listed in Table 1 or 2 | 25 g |
| Sorpol ® i.e., surfactant (available from Toho Chemical Industry Co., Ltd. | 10 g |
| Xylene | Balance |

The nonmedical fungicide according to the present invention can be preferably used in an amount of 50 to 1000 g, in terms of an active ingredient, per 10 are (a) when the fungicide is sprayed to the field having growing crops thereon and 0.5 to 8 kg, in terms of an active ingredient, per 10 are (a), when the fungicide is applied into the soil. It should be, of course, noted that the amount of the active ingredient depends upon the kinds of crops, diseases, and damages, seasons, weathers, and the preparation forms of the fungicides.

The nonmedical fungicides according to the present invention were evaluated in the following Test Examples.

TEST EXAMPLE 1

Evaluation test of antifungal activity against black spot of pear

A sample solution diluted to a predetermined concentration was uniformly sprayed on the developed leaves of pear trees (variety: Nijyusseiki) with an amount of 20 ml per 5 leaves, which were dried in a room.

After air drying, conidia of *Alternaria kikuchiana* formed on an apricot culture medium were inoculated on the leaves by spraying. The incubation was carried out at a temperature of 25° C. and a relative humidity (R.H.) of 100% for 3 days. After 3 days, the infected area was measured. Five tests were carried out in each run.

The results are shown in Table 4.

TABLE 4

| Compound No. | Concentration (a.i. ppm) | Average infected area (%) | Controlled value (%) | Chemical injury |
|---|---|---|---|---|
| 4 | 500 | 13.5 | 86.5 | — |
| 24 | 500 | 20.3 | 79.7 | — |
| 28 | 500 | 16.4 | 83.6 | — |
| 29 | 500 | 12.9 | 87.1 | — |
| 41 | 500 | 8.7 | 91.3 | — |
| 44 | 500 | 7.0 | 93.0 | — |
| 45 | 500 | 6.8 | 93.2 | — |
| 46 | 500 | 7.8 | 92.2 | — |
| 47 | 500 | 6.9 | 93.1 | — |
| 49 | 500 | 16.6 | 83.4 | — |
| 50 | 500 | 18.2 | 81.8 | — |
| 51 | 500 | 20.4 | 79.6 | — |
| iprodione[*1] | 500 | 7.1 | 92.9 | — |
| Control[*2] | — | 100 | — | — |

[*1]available from Phone-Poulenc
[*2]No treatment

TEST EXAMPLE 2

Evaluation test of antifungal activity against sheath blight of rice

A sample solution containing a predetermined concentration of the active compound was sprayed on cotyledons of a kidney bean (variety: Masterpiece), which were dried in a room.

After air drying the mycelia of *Rhizoctonia solani* IA grown on a PDA culture was inoculated after punching with a 8 mm$\phi$ cork borer. The incubation was carried out at a temperature of 2 8° C. and an R.H. of 100% for 3 days under dark conditions. The infected area was measured. Five tests were carried out in each run.

The results are shown in Table 5.

TABLE 5

| Compound No. | Concentration (a.i. ppm) | Average infected area (%) | Controlled value (%) | Chemical injury |
|---|---|---|---|---|
| 1 | 500 | 0 | 100 | — |
| 2 | 500 | 8 | 92 | — |
| 3 | 500 | 10 | 90 | — |
| 4 | 500 | 17 | 83 | — |
| 6 | 500 | 11 | 89 | — |
| 7 | 500 | 0 | 100 | — |
| 8 | 500 | 0 | 100 | — |
| 9 | 500 | 19 | 81 | — |
| 10 | 500 | 13 | 87 | — |
| 11 | 500 | 21 | 79 | — |
| 12 | 500 | 9 | 91 | — |
| 15 | 500 | 12 | 88 | — |
| 18 | 500 | 7 | 93 | — |
| 19 | 500 | 11 | 89 | — |
| 20 | 500 | 23 | 77 | — |
| 23 | 500 | 18 | 82 | — |
| 25 | 500 | 22 | 78 | — |
| 26 | 500 | 8 | 92 | — |
| 31 | 500 | 12 | 88 | — |
| 32 | 500 | 0 | 100 | — |
| 33 | 500 | 7 | 93 | — |
| 34 | 500 | 9 | 91 | — |
| 41 | 500 | 13 | 87 | — |
| 42 | 500 | 8 | 92 | — |
| 44 | 500 | 24 | 76 | — |
| 49 | 500 | 28 | 72 | — |
| Validacin ®[*1] | 500 | 25 | 75 | — |
| Control[*2] | 500 | 100 | — | — |

[*1]validanyicine A available from Takeda Chemical Industries, Ltd.
[*2]No treatment

TEST EXAMPLE 3

Evaluation test of antifungal effect against rice blast disease

A sample liquid agent containing a predetermined amount of the active solution was sprayed on rice seedlings (variety: Jyukkoku) at 3 leaf stage in a pot with the volume of 200 liter/10 a and the treated rice seedlings were air-dried.

After air drying, a spore suspension previously prepared in such a way that 40 conidia of rice blast fungus were present in a visual area of a 100 magnification microscope was inoculated by spraying. Immediately, the sprayed rice seedlings were allowed to stand under a dark condition of a temperature of 23° C. and an R.H. of 100%. After 48 hour inoculation, the rice seedlings were transferred to a green house and, after 10 days from the inocuration, the degree of the infection was measured. The protection value was calculated as follows. Three tests were carried out in each run.

$$\text{Degree of infection} = \frac{\Sigma nf}{4N} \times 100$$

wherein
n: Number of leaves in each infection degree
f: Index of infection degree
N: Number of leaves examined

| Index of infection degree | Number of lesion per leaf |
|---|---|
| 0 | 0 |
| 1 | 1 |
| 2 | 2-5 |
| 3 | 6-10 |
| 4 | 11 or more |

The results are shown in Table 6.

TABLE 6

| Compound No. | Concentration (a.i.ppm) | No. of leaves examined | No. of leaves in each infection degree | | | | | % of infected leaves | Infection degree | Chemical injury |
| | | | 0 | 1 | 2 | 3 | 4 | | | |
|---|---|---|---|---|---|---|---|---|---|---|
| 3 | 500 | 193 | 142 | 35 | 16 | 0 | 0 | 35.9 | 8.7 | — |
| 24 | 500 | 175 | 150 | 24 | 1 | 0 | 0 | 14.3 | 3.7 | — |
| 27 | 500 | 198 | 164 | 33 | 1 | 0 | 0 | 17.2 | 4.4 | — |
| 47 | 500 | 201 | 173 | 26 | 2 | 0 | 0 | 13.9 | 3.7 | — |
| FUJIONE ® | 500 | 196 | 138 | 45 | 13 | 0 | 0 | 29.6 | 9.1 | — |
| phthalide | 500 | 206 | 175 | 30 | 1 | 0 | 0 | 15.0 | 3.9 | — |
| Control[*3] | — | 188 | 0 | 0 | 67 | 79 | 42 | 100 | 71.7 | — |

[*1]Diisopropyl 1,3-dithiolan-2-ylidenemalonate available from Nihon Nohyaku Co., Ltd.
[*2]Available from Kureha Chemical Industry Co., Ltd.
[*3]No treatment

TEST EXAMPLE 4

Evaluation test of antifungal activity against leaf rust of wheat

A spore suspension previously prepared in such a way that 20 spores of *Puccinia recondita* f. sp. *tritici* were present in a visual area of 100 magnification microscope was sprayed on wheat seedlings (variety: Norin #61) at 2 leaf stage in a pot.

Immediately after inoculation, the sprayed wheat seedlings were allowed to stand under a dark condition at a temperature of 23° C. in an R.H. of 100% for 28 hours. After 28 hours, the wheat seedlings were transferred to a green house and, after 3 days from the inocuration, a sample fungicide solution containing a predetermined amount of the active compound was sprayed on the wheat seedlings with the volume of 200 liter/10 a. After 10 days from the inoculation, the degree of the infection was calculated as follows. Five tests were carried out in each run.

$$\text{Degree of infection} = \frac{\Sigma nf}{5N} \times 100$$

wherein
n: Number of leaves in each infection degree
f: Index of infection degree
N: Number of leaves examined.

| Index of infection degree | Area of infection (%) |
|---|---|
| 0 (No infection) | 0 |
| 1 (Low infection) | 1–25 |
| 3 (Medium infection) | 26–50 |
| 5 (Large infection) | 51–100 |

The results are shown in Table 7.

TEXT EXAMPLE 5

Evaluation test of antifungal activity against powdery mildew of cucumber

A sample solution containing a predetermined amount of the active compound was sprayed on cucumber seedlings (variety: Sagami Hanjiro) at 2 leaf stage in a pot with the volume of 200 liter/10 a and the treated cucumber seedlings were air-dried in a room.

After air drying, the treated cucumber seedlings was allowed to stand in a green house to naturally infect with the spores of *Sphaerotheca fuliginea*.

After 14 days, the degree of the infection was calculated according to the following criteria. Five test were carried out in each run and ten leaves were evaluated.

$$\text{Degree of infection} = \frac{\Sigma nf}{5N} \times 100$$

wherein
n: Number of leaves in each infection degree
f: Index of infection degree
N: Number of leaves examined.

| Index of infection degree | Infected area (%) |
|---|---|
| 0 (No infection) | 0 |
| 1 (Low infection) | 1–25 |
| 3 (Medium infection) | 26–50 |
| 5 (Large infection) | 51–100 |

The results are shown in Table 8.

TABLE 7

| Compound No. | Concentration (a.i.ppm) | No. of leaves examined | No. of leaves in each infection degree 0 | 1 | 3 | 5 | % of infected area | Infection degree | Chemical injury |
|---|---|---|---|---|---|---|---|---|---|
| 18 | 20 | 10 | 10 | 0 | 0 | 0 | 0 | 0 | — |
| 23 | 20 | 10 | 10 | 0 | 0 | 0 | 0 | 0 | — |
| 54 | 20 | 10 | 10 | 0 | 0 | 0 | 0 | 0 | — |
| triadimefon*[1] | 20 | 10 | 10 | 0 | 0 | 0 | 0 | 0 | — |
| Control*[2] | — | 10 | 0 | 0 | 0 | 10 | 100 | 100 | — |

*[1] available from Bayer AG
*[2] No treatment

TABLE 8

| Compound No. | Concentration (a.i. ppm) | No. of leaves examined | No. of leaves in each infection degree 0 | 1 | 3 | 5 | % of infected leaves | Infection degree | Chemical injury |
|---|---|---|---|---|---|---|---|---|---|
| 1 | 50 | 10 | 10 | 0 | 0 | 0 | 0 | 0 | — |
| 2 | 50 | 10 | 10 | 0 | 0 | 0 | 0 | 0 | — |
| 3 | 50 | 10 | 10 | 0 | 0 | 0 | 0 | 0 | — |
| 4 | 50 | 10 | 10 | 0 | 0 | 0 | 0 | 0 | — |
| 5 | 50 | 10 | 10 | 0 | 0 | 0 | 0 | 0 | — |
| 6 | 50 | 10 | 10 | 0 | 0 | 0 | 0 | 0 | — |
| 7 | 50 | 10 | 10 | 0 | 0 | 0 | 0 | 0 | — |
| 8 | 50 | 10 | 10 | 0 | 0 | 0 | 0 | 0 | — |
| 9 | 50 | 10 | 10 | 0 | 0 | 0 | 0 | 0 | — |
| 10 | 50 | 10 | 10 | 0 | 0 | 0 | 0 | 0 | — |
| 11 | 50 | 10 | 10 | 0 | 0 | 0 | 0 | 0 | — |
| 12 | 50 | 10 | 10 | 0 | 0 | 0 | 0 | 0 | — |
| 13 | 50 | 10 | 10 | 0 | 0 | 0 | 0 | 0 | — |
| 14 | 50 | 10 | 10 | 0 | 0 | 0 | 0 | 0 | — |
| 15 | 50 | 10 | 10 | 0 | 0 | 0 | 0 | 0 | — |
| 16 | 50 | 10 | 10 | 0 | 0 | 0 | 0 | 0 | — |
| 17 | 50 | 10 | 10 | 0 | 0 | 0 | 0 | 0 | — |
| 18 | 50 | 10 | 10 | 0 | 0 | 0 | 0 | 0 | — |
| 19 | 50 | 10 | 10 | 0 | 0 | 0 | 0 | 0 | — |

TABLE 8-continued

| Compound No. | Concentration (a.i. ppm) | No. of leaves examined | No. of leaves in each infection degree | | | | % of infected leaves | Infection degree | Chemical injury |
|---|---|---|---|---|---|---|---|---|---|
| | | | 0 | 1 | 3 | 5 | | | |
| 20 | 50 | 10 | 10 | 0 | 0 | 0 | 0 | 0 | — |
| 21 | 50 | 10 | 10 | 0 | 0 | 0 | 0 | 0 | — |
| 22 | 50 | 10 | 10 | 0 | 0 | 0 | 0 | 0 | — |
| 23 | 50 | 10 | 10 | 0 | 0 | 0 | 0 | 0 | — |
| 24 | 50 | 10 | 10 | 0 | 0 | 0 | 0 | 0 | — |
| 25 | 50 | 10 | 10 | 0 | 0 | 0 | 0 | 0 | — |
| 26 | 50 | 10 | 8 | 2 | 0 | 0 | 20 | 4 | — |
| 27 | 50 | 10 | 10 | 0 | 0 | 0 | 0 | 0 | — |
| 28 | 50 | 10 | 10 | 0 | 0 | 0 | 0 | 0 | — |
| 29 | 50 | 10 | 10 | 0 | 0 | 0 | 0 | 0 | — |
| 30 | 50 | 10 | 10 | 0 | 0 | 0 | 0 | 0 | — |
| 31 | 50 | 10 | 10 | 0 | 0 | 0 | 0 | 0 | — |
| 32 | 50 | 10 | 10 | 0 | 0 | 0 | 0 | 0 | — |
| 33 | 50 | 10 | 10 | 0 | 0 | 0 | 0 | 0 | — |
| 34 | 50 | 10 | 10 | 0 | 0 | 0 | 0 | 0 | — |
| 35 | 50 | 10 | 10 | 0 | 0 | 0 | 0 | 0 | — |
| 36 | 50 | 10 | 10 | 0 | 0 | 0 | 0 | 0 | — |
| 37 | 50 | 10 | 10 | 0 | 0 | 0 | 0 | 0 | — |
| 38 | 50 | 10 | 10 | 0 | 0 | 0 | 0 | 0 | — |
| 39 | 50 | 10 | 10 | 0 | 0 | 0 | 0 | 0 | — |
| 40 | 50 | 10 | 10 | 0 | 0 | 0 | 0 | 0 | — |
| 41 | 50 | 10 | 8 | 2 | 0 | 0 | 20 | 4 | — |
| 42 | 50 | 10 | 8 | 2 | 0 | 0 | 20 | 4 | — |
| 43 | 50 | 10 | 10 | 0 | 0 | 0 | 0 | 0 | — |
| 44 | 50 | 10 | 8 | 2 | 0 | 0 | 20 | 4 | — |
| 45 | 50 | 10 | 10 | 0 | 0 | 0 | 0 | 0 | — |
| 46 | 50 | 10 | 10 | 0 | 0 | 0 | 0 | 0 | — |
| 48 | 50 | 10 | 10 | 0 | 0 | 0 | 0 | 0 | — |
| 49 | 50 | 10 | 10 | 0 | 0 | 0 | 0 | 0 | — |
| 51 | 50 | 10 | 8 | 2 | 0 | 0 | 20 | 4 | — |
| 53 | 50 | 10 | 8 | 2 | 0 | 0 | 20 | 4 | — |
| 55 | 50 | 10 | 8 | 2 | 0 | 0 | 20 | 4 | — |
| triadimefon*[1] | 50 | 10 | 10 | 0 | 0 | 0 | 0 | 0 | — |
| Control*[2] | 50 | 10 | 0 | 0 | 2 | 8 | 100 | 92 | — |

*[1] Available from Bayer AG
*[2] No treatment

TEST EXAMPLE 6

Evaluation test of antifungal activity against gray mold of cucumber

A sample solution containing a predetermined amount of the active compound was sprayed on cucumber seedlings (variety: Suhyoo) at 3 leaf stage in a pot at a volume of 200 liter/10 a and the treated cucumber seedlings were air-dried for 24 hours in a room.

After air drying, a spore suspension was prepared in such a way that 100 conidia of Botrytis cinerea were present in a visual area of a 100 magnification microscope and a commercially available yeast extract (1% amount) and a commercially available glucose (10% amount) were added thereto. The resultant suspension was inoculated by spraying. Immediately, the sprayed cucumber were allowed to stand under a dark condition at a temperature of 22° C. and an R.H. of 100%. After 3 days, the degree of the infection was measured. The protection value was calculated as follows. Eight tests were carried out in each run.

$$\text{Degree of infection} = \frac{\Sigma nf}{5N} \times 100$$

wherein
n: Number of leaves in each infection degree
f: Index of refraction degree
N: Number of leaves examined

| Index of infection degree | Infected area (%) |
|---|---|
| 0 (No infection) | 0 |
| 1 (Low infection) | 1–25 |
| 3 (Medium infection) | 26–50 |
| 5 (Large infection) | 51–100 |

The results are shown in Table 9.

TABLE 9

| Compound No. | Concentration (a.i. ppm) | No. of leaves examined | No. of leaves in each infection degree | | | | % of infected leaves | Infection degree | Chemical injury |
|---|---|---|---|---|---|---|---|---|---|
| | | | 0 | 1 | 3 | 5 | | | |
| 72 | 500 | 24 | 10 | 14 | 0 | 0 | 58.3 | 11.7 | — |
| 73 | 500 | 24 | 11 | 13 | 0 | 0 | 54.2 | 10.8 | — |
| 74 | 500 | 24 | 9 | 15 | 0 | 0 | 62.5 | 12.5 | — |
| chlorothanlonil*[1] | 1250 | 24 | 4 | 20 | 0 | 0 | 83.3 | 16.7 | — |
| iprodione*[2] | 500 | 24 | 6 | 18 | 0 | 0 | 75.0 | 15.0 | — |
| Control*[3] | — | 24 | 0 | 0 | 0 | 24 | 100 | 100 | — |

*[1] available from SDS Biotech K.K.
*[2] available from Rhone-Poulenc
*[3] No treatment

TEST EXAMPLE 7

Evaluation test of antifungal effect against rice Helminthosporium leaf spot

A sample solution containing a predetermined amount of the active compound was sprayed on rice seedlings (variety: Jyukkoku) at 5 leaf stage in a pot at a volume of 200 liter/10 a and the treated rice seedlings were air-dried in a room.

After air-drying, a spore suspension previously prepared in such a way that 10 conidia of *Helminthosporium oryzae* were present in a visual area of a 100 magnification microscope was inoculated by spraying.

Immediately, the sprayed rice seedlings were allowed to stand under a dark condition at a temperature of 28° C. and an R.H. of 100%. After 24 hours, the rice seedlings were transferred to a green house and, after 7 days from the inoculation, the degree of the infection was measured. The protection value was calculated as follows. Five tests were carried out in each run.

$$\text{Degree of infection} = \frac{\Sigma nf}{4N} \times 100$$

wherein
n: Number of leaves in each infection degree
f: Index of infection degree
N: Number of leaves examined

| Index of infection degree | Number of lesion per leaf |
|---|---|
| 0 | 0 |
| 1 | 1 |
| 2 | 2–5 |
| 3 | 6–10 |
| 4 | 11 or more |

The results are shown in Table 10.

TABLE 10

| Compound No. | Concentration (a.i. ppm) | No. of leaves examined | No. of leaves in each infection degree | | | | | % of infected leaves | Infection degrees | Chemical injury |
|---|---|---|---|---|---|---|---|---|---|---|
| | | | 0 | 1 | 2 | 3 | 4 | | | |
| 72 | 500 | 270 | 145 | 83 | 42 | 0 | 0 | 46.3 | 15.5 | — |
| 73 | 500 | 270 | 147 | 85 | 38 | 0 | 0 | 45.5 | 14.9 | — |
| 74 | 500 | 270 | 151 | 75 | 44 | 0 | 0 | 44.1 | 15.9 | — |
| iprodione[*1] | 500 | 270 | 143 | 81 | 46 | 0 | 0 | 47.0 | 16.0 | — |
| chlorothalonil[*2] | 300 | 270 | 149 | 78 | 43 | 0 | 0 | 44.8 | 15.2 | — |
| Control[*3] | — | 270 | 0 | 0 | 10 | 63 | 197 | 100 | 92.3 | — |

[*1] available from Rhone-Poulenc
[*2] available from SDS Biotech K.K.
[*3] No treatment

TEST EXAMPLE 8

Antifungal spectrum test against conidium by agar dilution method

A 10 ml amount of a potato-agar medium containing a predetermined concentration of each active ingredient was poured into a petri dish. After solidifying, the tip portion of the flora of each test microorganism previously incubated on a plate culture medium, which was punched with a 8 cm$\phi$ cork borer, was inoculated on the culture medium containing the active ingredient. The culture medium thus obtained was allowed to stand in a constant temperature room for predetermined days. Thereafter, the growth of mycelium of the microorganism was measured and the MIC was determined. Four tests were carried out in each run.

The microorganisms used are as follows.
A: *Alternaria kikuchiana*
B: *Rhizoctonia solani IA*
C: *Helminthosporium oryzae*
D: *Botrytis cinerea*
E: *Sclerotinia sclerotiorum*
F: *Phytophthora infestans*
G: *Cercospora kikuchii*
H: *Venturia nashicola*

The tests for microorganisms A to G were carried out at a temperature of 25° C. for 5 days, and the test for microorganism H was carried out at a temperature of 20° C. for 20 days.

The results are shown in Table 11.

TABLE 11

| Compound No. | MIC (ppm) Microorganism | | | | | | | |
|---|---|---|---|---|---|---|---|---|
| | A | B | C | D | E | F | G | H |
| 72 | 10 | 2 | 1 | 5 | 5 | 10 | 2 | 2 |
| 73 | 10 | 2 | 1 | 5 | 5 | 10 | 1 | 2 |
| 74 | 10 | 1 | 1 | 5 | 5 | 10 | 1 | 1 |

TEST EXAMPLE 9

Antifungal spectrum test against conidium by agar dilution method

A 10 ml amount of a potato-agar medium containing a predetermined concentration of each active ingredient was poured into a petri dish. After solidifying, the tip portion of the flora of each test microorganism previously incubated on a plate culture medium, which was punched with a 8 cm$\phi$ cork borer, was inoculated on the culture medium containing the active ingredient. The culture medium thus obtained was allowed to stand in a constant temperature room for predetermined days. Thereafter, the growth of mycelium of the microorganism was measured and the MIC was determined. Four tests were carried out in each run.

The microorganisms used are as follows.
A: *Alternaria kikuchiana*
B: *Rhizoctonia solani IA*
C: *Helminthosporium oryzae*
D: *Botrytis cinerea*
E: *Sclerotinia sclerotiorum*
F: *Phytophthora infestans*
G: *Cercospora kikuchii*
H: *Venturia nashicola*

The tests for microorganisms A to G were carried out at a temperature of 25° C. for 5 days, and the test for microorganism H was carried out at a temperature of 20° C. for 20 days.

The results are shown in Table 12.

TABLE 12

| Compound No. | MIC (ppm) Microorganism | | | | | | | |
|---|---|---|---|---|---|---|---|---|
| | A | B | C | D | E | F | G | H |
| 75 | 10 | 5 | 2 | 5 | 5 | 10 | 2 | 2 |
| 76 | 10 | 10 | 5 | 10 | 10 | 10 | 5 | 5 |
| 77 | 10 | 5 | 5 | 5 | 5 | 10 | 5 | 5 |
| 78 | 10 | 2 | 1 | 5 | 5 | 10 | 1 | 1 |
| 79 | 10 | 2 | 1 | 5 | 5 | 10 | 1 | 1 |
| 80 | 10 | 5 | 2 | 5 | 5 | 10 | 2 | 2 |
| 81 | 10 | 5 | 5 | 5 | 5 | 10 | 5 | 5 |
| 82 | 10 | 5 | 5 | 10 | 10 | 20 | 10 | 10 |
| 83 | 10 | 5 | 5 | 10 | 10 | 20 | 10 | 10 |
| 84 | 10 | 5 | 5 | 5 | 5 | 10 | 5 | 5 |
| 85 | 10 | 10 | 10 | 10 | 10 | 10 | 10 | 10 |
| 86 | 10 | 5 | 5 | 5 | 5 | 10 | 5 | 5 |

TEST EXAMPLE 10

Evaluation test of antifungal activity against black spot of pear

A sample solution diluted to a predetermined concentration was uniformly sprayed on the developed leaves of pear trees (variety: Nijyusseiki) with a volume of 20 ml per 5 leaves, which were dried in a room.

After air drying, conidia of *Alternaria kikuchiana* formed on an apricot culture medium were inoculated on the leaves by spraying. The incubation was carried out at a temperature of 25° C. and an R.H. of 100% for 3 days. After 3 days, the infected area was measured. Five tests were carried out in each run.

The results are shown in Table 13.

TABLE 13

| Compound No. | Concentration (a.i. ppm) | Average infected area (%) | Controlled value (%) | Chemical injury |
|---|---|---|---|---|
| 75 | 500 | 7.3 | 92.7 | — |
| 76 | 500 | 8.5 | 91.5 | — |
| 77 | 500 | 16.7 | 83.3 | — |
| 78 | 500 | 6.9 | 93.1 | — |
| 79 | 500 | 7.1 | 92.9 | — |
| 80 | 500 | 8.0 | 92.0 | — |
| 81 | 500 | 17.1 | 82.9 | — |
| 82 | 500 | 15.3 | 84.7 | — |
| 83 | 500 | 17.2 | 82.8 | — |
| 84 | 500 | 7.0 | 93.0 | — |
| 85 | 500 | 8.0 | 92.0 | — |
| 86 | 500 | 10.1 | 89.9 | — |
| iprodione*[1] | 500 | 7.0 | 93.0 | — |
| Control*[2] | — | 100 | — | — |

*[1]available from Rhone-Poulenc
*[2]No treatment

TEST EXAMPLE 11

Evaluation test of antifungal activity against sheath blight of rice

A sample solution containing a predetermined concentration of the active compound was sprayed on cotyledons of a kidney bean (variety: *Masterpiece*), which were dried in a room.

After air-drying, the mycelia of *Rhizoctonia solani* IA grown on a PDA culture medium were inoculated after punching with a 8 mmφ cork borer. The incubation was carried out at a temperature of 28° C. and an R.H. of 100% for 3 days under a dark condition. The infected area was measured. Five leaves were used in each treatment and four tests were carried out in each run.

The results are shown in Table 14.

TABLE 14

| Compound No. | Concentration (a.i. ppm) | Average infected area (%) | Controlled value (%) | Chemical injury |
|---|---|---|---|---|
| 75 | 500 | 21 | 79 | — |
| 76 | 500 | 45 | 55 | — |
| 77 | 500 | 23 | 77 | — |
| 78 | 500 | 18 | 82 | — |
| 79 | 500 | 16 | 84 | — |
| 80 | 500 | 20 | 80 | — |
| 82 | 500 | 40 | 60 | — |
| 83 | 500 | 43 | 57 | — |
| 84 | 500 | 17 | 83 | — |
| 85 | 500 | 23 | 77 | — |
| 86 | 500 | 18 | 82 | — |
| iprodione*[1] | 500 | 20 | 80 | — |
| Control*[2] | — | 100 | — | — |

*[1]available from Rhone-Poulenc
*[2]No treatment

TEST EXAMPLE 12

Evaluation test of antifungal activity against leaf rust of wheat

A sample solution containing a predetermined amount of the active compound was sprayed on wheat seedlings (variety: Nohrin #61) at 2 leaf stage in a pot with the volume of 200 liter/10 a and the treated wheat seedlings were air-dried.

After air-drying, a spore suspension previously prepared in such a way that 20 spores of *Puccinia recondita* f. sp. *tritici* were present in a visual area of a 100 magnification microscope was inoculated by spraying.

Immediately after inoculation, the sprayed wheat seedlings were allowed to stand under a dark condition at a temperature of 23° C. and an R.H. of 100% for 28 hours. After 28 hours, the wheat seedlings were transferred to a green house and, after 10 days from the inoculation, the degree of the infection was calculated as follows.

Five tests were carried out in each run.

$$\text{Degree of infection} = \frac{\Sigma nf}{5N} \times 100$$

wherein
n: Number of leaves in each infection degree
f: Index of infection degree
N: Number of leaves examined.

| Index of infection degree | Infected area (%) |
|---|---|
| 0 (No infection) | 0 |
| 1 (Low infection) | 1–25 |
| 3 (Medium infection) | 26–50 |
| 5 (Large infection) | 51–100 |

The results are shown in Table 15.

TABLE 15

| Compound No. | Concentration (a.i. ppm) | No. of leaves examined | No. of leaves in each infection degree | | | % of infected leaves | Infection degree | Chemical injury |
|---|---|---|---|---|---|---|---|---|
| | | | 0 | 1 | 3 | 5 | | | |
| 75 | 200 | 50 | 50 | 0 | 0 | 0 | 0 | 0 | — |
| 76 | 200 | 50 | 50 | 0 | 0 | 0 | 0 | 0 | — |

TABLE 15-continued

| Compound No. | Concentration (a.i. ppm) | No. of leaves examined | No. of leaves in each infection degree | | | | % of infected leaves | Infection degree | Chemical injury |
|---|---|---|---|---|---|---|---|---|---|
| | | | 0 | 1 | 3 | 5 | | | |
| 77 | 200 | 50 | 50 | 0 | 0 | 0 | 0 | 0 | — |
| 78 | 200 | 50 | 50 | 0 | 0 | 0 | 0 | 0 | — |
| 79 | 200 | 50 | 50 | 0 | 0 | 0 | 0 | 0 | — |
| 80 | 200 | 50 | 50 | 0 | 0 | 0 | 0 | 0 | — |
| 81 | 200 | 50 | 50 | 0 | 0 | 0 | 0 | 0 | — |
| 82 | 200 | 50 | 50 | 0 | 0 | 0 | 0 | 0 | — |
| 83 | 200 | 50 | 50 | 0 | 0 | 0 | 0 | 0 | — |
| 84 | 200 | 50 | 50 | 0 | 0 | 0 | 0 | 0 | — |
| 85 | 200 | 50 | 50 | 0 | 0 | 0 | 0 | 0 | — |
| 86 | 200 | 50 | 50 | 0 | 0 | 0 | 0 | 0 | — |
| triadimefon[1] | 100 | 50 | 50 | 20 | 0 | 0 | 0 | 0 | — |
| Control[2] | — | 50 | 0 | 0 | 21 | 29 | 100 | 83.2 | — |

[1] available from Bayer AG
[2] No treatment

TEST EXAMPLE 13

Evaluation test of antifungal activity against powdery mildew of cucumber

A sample solution agent containing a predetermined amount of the active compound was sprayed on cucumber seedlings (variety: Sagami hanjiro) at 2 leaf stage in a pot at a volume of 200 liter/10 a and the treated cucumber seedlings were air-dried in a room.

After air drying, the treated cucumber seedlings were allowed to stand in a green house to naturally infect with the conidia of *Sphaerotheca fuliginea*.

After 14 days, the degree of the infection was calculated according to the following criteria. Five tests were carried out in each run and ten leaves were evaluated.

$$\text{Degree of infection} = \frac{\Sigma nf}{5N} \times 100$$

wherein
n: Number of leaves in each infection degree
f: Index of infection degree
N: Number of leaves examined.

| Index of infection degree | Infected area (%) |
|---|---|
| 0 (No infection) | 0 |
| 1 (Low infection) | 1-25 |
| 3 (Medium infection) | 26-50 |
| 5 (Large infection) | 51-100 |

The results are shown in Table 16

TEST EXAMPLE 14

Evaluation test of antifungal activity against gray mold of cucumber

A sample solution containing a predetermined amount of the active compound was sprayed on cucumber seedlings (variety: Suhyo) at 3 leaf stage in a pot at a volume of 200 liter/10 a and the treated cucumber seedlings were air-dried for 24 hours in a room.

After air drying, a spore suspension was prepared in such a way that 100 conidia of *Botrytis cinerea* were present in a visual area of a 100 magnification microscope and a commercially available yeast extract (1% amount) and a commercially available glucose (10% amount) were added thereto. The resultant suspension was sprayed for inoculation. Immediately, the sprayed cucumber seedlings were allowed to stand under a dark condition at a temperature of 22° C. and an R.H. of 100%. After 3 days, the degree of the infection was measured. The protection value was calculated as follows. Eight tests were carried out in each run.

$$\text{Degree of infection} = \frac{\Sigma nf}{5N} \times 100$$

wherein
n: Number of leaves in each infection degree
f: Index of infection degree
N: Number of leaves examined.

TABLE 16

| Compound No. | Concentration (a.i. ppm) | No. of leaves examined | No. of leaves in each infection degree | | | | % of infected leaves | Infection degree | Chemical injury |
|---|---|---|---|---|---|---|---|---|---|
| | | | 0 | 1 | 3 | 5 | | | |
| 75 | 50 | 10 | 10 | 0 | 0 | 0 | 0 | 0 | — |
| 76 | 50 | 10 | 10 | 0 | 0 | 0 | 0 | 0 | — |
| 77 | 50 | 10 | 10 | 0 | 0 | 0 | 0 | 0 | — |
| 78 | 50 | 10 | 10 | 0 | 0 | 0 | 0 | 0 | — |
| 79 | 50 | 10 | 10 | 0 | 0 | 0 | 0 | 0 | — |
| 80 | 50 | 10 | 10 | 0 | 0 | 0 | 0 | 0 | — |
| 81 | 50 | 10 | 10 | 0 | 0 | 0 | 0 | 0 | — |
| 82 | 50 | 10 | 10 | 0 | 0 | 0 | 0 | 0 | — |
| 83 | 50 | 10 | 10 | 0 | 0 | 0 | 0 | 0 | — |
| 84 | 50 | 10 | 10 | 0 | 0 | 0 | 0 | 0 | — |
| 85 | 50 | 10 | 10 | 0 | 0 | 0 | 0 | 0 | — |
| 86 | 50 | 10 | 10 | 0 | 0 | 0 | 0 | 0 | — |
| triadimefon[1] | 50 | 10 | 10 | 0 | 0 | 0 | 0 | 0 | — |
| Control[2] | — | 10 | 0 | 0 | 0 | 10 | 100 | 100 | — |

[1] see Table 15.
[2] No treatment

| Index of infection degree | Infected area (%) |
|---|---|
| 0 (No infection) | 0 |
| 1 (Low infection) | 1–25 |
| 3 (Medium infection) | 26–50 |
| 5 (Large infection) | 51–100 |

The results are shown in Table 17.

TABLE 17

| Compound No. | Concentration (a.i. ppm) | No. of leaves examined | No. of leaves in each infection degree 0 | 1 | 3 | 5 | % of infected leaves | Infection degree | Chemical injury |
|---|---|---|---|---|---|---|---|---|---|
| 75 | 500 | 24 | 7 | 17 | 0 | 0 | 70.8 | 14.2 | — |
| 76 | 500 | 24 | 1 | 18 | 5 | 0 | 95.8 | 27.5 | — |
| 77 | 500 | 24 | 8 | 15 | 1 | 0 | 66.7 | 15.0 | — |
| 78 | 500 | 24 | 10 | 14 | 0 | 0 | 58.3 | 11.7 | — |
| 79 | 500 | 24 | 4 | 19 | 1 | 0 | 83.3 | 18.3 | — |
| 80 | 500 | 24 | 6 | 18 | 0 | 0 | 75.0 | 15.0 | — |
| 82 | 500 | 24 | 1 | 19 | 4 | 0 | 95.8 | 25.8 | — |
| 83 | 500 | 24 | 0 | 21 | 3 | 0 | 100 | 25.0 | — |
| 84 | 500 | 24 | 3 | 19 | 2 | 0 | 87.5 | 20.8 | — |
| 85 | 500 | 24 | 1 | 18 | 5 | 0 | 95.8 | 27.5 | — |
| 86 | 500 | 24 | 4 | 19 | 1 | 0 | 83.3 | 18.3 | — |
| iprodione*[1] | 500 | 24 | 6 | 18 | 0 | 0 | 75.0 | 15.0 | — |
| Control*[2] | — | 24 | 0 | 0 | 0 | 24 | 100 | 100 | — |

*[1] available from Rhone-Poulenc
*[2] No treatment

TEST EXAMPLE 15

Evaluation test of antifungal activity against brown rot of eggplant

A sample solution diluted to a predetermined concentration was uniformly sprayed on the four developed leaves of eggplant seedlings (variety: Senryo #2) in a pot with an amount of 10 ml per 4 leaves and the treated eggplant seedlings were dried for 24 hours in a room.

After the 24 hours air drying, a suspension of zoospore of *Phytophthora capsici* previously prepared in such a way that 30 zoospores were present in a visual area of a 100 magnification microscope. Immediately, the sprayed eggplant seedlings were allowed to stand under a dark condition at a temperature of 25° C. and an R.H. of 100%. After 2 days, the infected area was measured. Four tests were carried out in each run.

The results are shown in Table 18.

TABLE 18

| Compound No. | Concentration (a.i. ppm) | Average infected area (%) | Controlled value (%) | Chemical injury |
|---|---|---|---|---|
| 75 | 500 | 10.5 | 89.5 | — |
| 76 | 500 | 50.0 | 50.0 | — |
| 77 | 500 | 15.5 | 84.5 | — |
| 78 | 500 | 12.0 | 88.0 | — |
| 79 | 500 | 7.5 | 92.5 | — |
| 80 | 500 | 20.0 | 80.0 | — |
| 81 | 500 | 35.0 | 65.0 | — |
| 82 | 500 | 45 | 55.0 | — |
| 83 | 500 | 50 | 50.0 | — |
| 84 | 500 | 10.5 | 89.5 | — |
| 85 | 500 | 7.5 | 92.5 | — |
| 86 | 500 | 13.5 | 86.5 | — |
| chlorothalonil*[1] | 500 | 13.5 | 86.5 | — |

TABLE 18-continued

| Compound No. | Concentration (a.i. ppm) | Average infected area (%) | Controlled value (%) | Chemical injury |
|---|---|---|---|---|
| Control*[2] | — | 100 | — | — |

*[1] available from SDS Biotech K.K.
*[2] No treatment

TEST EXAMPLE 16

Evaluation test of antifungal activity against late blight of tomato

A sample solution diluted to a predetermined concentration was uniformly sprayed on tomato seedlings (variety: Oogata Fukuju) at 5 leaf stage in a pot with an amount of 200 liter/10 a and the treated tomato seedlings were dried for 24 hours in a room.

After the 24 hour air drying, a zoospore suspension of *Phytophthora infestans* previously prepared in such a way that 5 zoospores were present in a visual area of a 100 magnification microscope was inoculated by spraying. Immediately after the inoculation, the sprayed tomato seedlings were allowed to stand under a dark condition at a temperature of 20° C. and an R.H. of 100%. After 7 days, the degree of the infection was measured. The protection value was calculated as follows. Six tests were carried out in each run:

$$\text{Degree of infection} = \frac{\Sigma nf}{4N} \times 100$$

wherein
n: Number of leaves in each infection degree
f: Index of infection degree
N: Number of leaves examined

| Index of infection degree | Number of lesion per leaf |
|---|---|
| 0 | 0 |
| 1 | 1 |
| 2 | 2–5 |
| 3 | 6–10 |
| 4 | 11 or more |

The results are shown in Table 19.

TABLE 19

| Compound No. | Concentration (a.i. ppm) | No. of leaves examined | No. of leaves in each infection degree | | | | | % of infected leaves | Infection degree | Chemical injury |
|---|---|---|---|---|---|---|---|---|---|---|
| | | | 0 | 1 | 2 | 3 | 4 | | | |
| 75 | 500 | 30 | 14 | 15 | 1 | 0 | 0 | 53.3 | 14.2 | — |
| 76 | 500 | 30 | 3 | 22 | 4 | 1 | 0 | 90.0 | 27.5 | — |
| 77 | 500 | 30 | 4 | 18 | 7 | 1 | 0 | 86.7 | 29.2 | — |
| 78 | 500 | 30 | 5 | 23 | 2 | 0 | 0 | 83.3 | 22.5 | — |
| 79 | 500 | 30 | 16 | 13 | 1 | 0 | 0 | 46.7 | 12.5 | — |
| 80 | 500 | 30 | 13 | 16 | 1 | 0 | 0 | 56.7 | 15.0 | — |
| 81 | 500 | 30 | 0 | 16 | 13 | 1 | 0 | 100 | 37.5 | — |
| 82 | 500 | 30 | 0 | 15 | 14 | 1 | 0 | 100 | 38.3 | — |
| 83 | 500 | 30 | 0 | 17 | 12 | 1 | 0 | 100 | 36.7 | — |
| 84 | 500 | 30 | 6 | 21 | 3 | 0 | 0 | 80.0 | 22.5 | — |
| 85 | 500 | 30 | 7 | 22 | 1 | 0 | 0 | 76.7 | 20.0 | — |
| 86 | 500 | 30 | 4 | 24 | 2 | 0 | 0 | 86.7 | 23.3 | — |
| mancozeb*[1] | 500 | 30 | 7 | 22 | 1 | 0 | 0 | 76.7 | 20.0 | — |
| Control*[2] | — | 30 | 0 | 0 | 3 | 8 | 19 | 100 | 88.3 | — |

*[1] available from Rohm and Haas Co.
*[2] No treatment

We claim:

1. A propionate derivative having the general formula (I):

$$R^1-CH-CH-CO_2-R^2 \quad (I)$$
$$\phantom{R^1-}|\phantom{CH-}|$$
$$\phantom{R^1-}R^3\phantom{H-}R^4$$

wherein $R^1$ is phenyl which may be substituted with one or more of the same or different substituents selected from the group consisting of halogen, methyl, methoxy, and nitro, $R^2$ is $C_1$-$C_6$ alkyl, $C_3$-$C_7$ cycloalkyl, or $C_3$-$C_6$ alkenyl, $R^3$ is $C_1$-$C_6$ alkylthio, $C_3$-$C_7$ cycloalkylthio, $C_3$-$C_6$ alkenylthio, phenylthio, or benzylthio group which may be substituted with halogen or methyl, and $R^4$ is imidazol-1-yl or 1,2,4-triazol-1-yl; or the acid addition salt thereof or the metal complex thereof.

2. A propionate derivative as claimed in claim 1, wherein $R^2$ in the general formula (I) is an alkyl group having 1 to 6 carbon atoms.

3. A propionate derivative as claimed in claim 1, wherein $R^3$ in the general formula (I) is an alkylthio group having 1 to 6 carbon atoms, a cycloalkylthio group having 3 to 7 carbon atoms, a phenylthio group, or benzylthio group which may be substituted with halogen or methyl.

4. A propionate derivative as claimed in claim 1, wherein said acid addition salt is derived from hydrochloric acid, hydrobromic acid, sulfuric acid, oxalic acid, or sulfonic acid.

5. A propionate derivative as claimed in claim 1, wherein said metal complex has the general formula (I'):

$$\left( R^1-CH-CH-CO_2-R^2 \atop \phantom{R^1-}|\phantom{CH-}|\phantom{-CO_2-R^2} \atop \phantom{R^1-}R^3\phantom{H-}R^4\phantom{-CO_2-R^2} \right)_n \cdot Z \quad (I')$$

wherein $R^1$, $R^2$, $R^3$, and $R^4$ are as defined in claim 1, Z is a metal salt, and n is an integer of 1 to 4.

6. A propionate derivative as claimed in claim 5, wherein Z in the general formula (I') is an inorganic acid salt of copper, cobalt, zinc, nickel, iron, or silver.

7. A nonmedical fungicide comprising, as an effective ingredient, a propionate derivative having the general formula (I) or an agriculturally acceptable salt thereof:

$$R^1-CH-CH-CO_2-R^2 \quad (I)$$
$$\phantom{R^1-}|\phantom{CH-}|$$
$$\phantom{R^1-}R^3\phantom{H-}R^4$$

wherein $R^1$ is phenyl which may be substituted with one or more of the same or different substituents selected from the group consisting of halogen, methyl, methoxy, and nitro, $R^2$ is $C_1$-$C_6$ alkyl, $C_3$-$C_7$ cycloalkyl, or $C_3$-$C_6$ alkenyl, $R^3$ is $C_1$-$C_6$ alkylthio, $C_3$-$C_7$ cycloalkylthio, $C_3$-$C_6$ alkenylthio, phenylthio, or benzylthio group which may be substituted with halogen or methyl and $R^4$ is imidazol-1-yl or 1,2,4-triazol-1-yl; or the acid addition salt thereof or the metal complex thereof.

8. A nonmedical fungicide as claimed in claim 7 containing 0.1% to 99.9% by weight of the propionate derivative.

9. A nonmedical fungicide as claimed in claim 7, wherein the propionate derivative has the general formula (I) wherein $R^1$ is phenyl which may be substituted with one or more of the same or different substituents selected from the group consisting of halogen, methyl, methoxy, and nitro, $R^2$ is alkyl having 1 to 6 carbon atoms, $R^3$ is alkylthio having 1 to 6 carbon atoms, cycloalkylthio having 3 to 7 carbon atoms, or phenylthio, and $R_4$ is imidazol-1-yl or 1,2,4-triazol-1-yl.

10. A nonmedical fungicide as claimed in claim 7, wherein said metal complex has the general formula (I'):

$$\left( R^1-CH-CH-CO_2-R^2 \atop \phantom{R^1-}|\phantom{CH-}|\phantom{-CO_2-R^2} \atop \phantom{R^1-}R^3\phantom{H-}R^4\phantom{-CO_2-R^2} \right)_n \cdot Z \quad (I')$$

wherein $R^1$, $R^2$, $R^3$, and $R^4$ are as defined in claim 7, Z is a metal salt, and n is an integer of 1 to 4.

* * * * *